(12) United States Patent
Golovchenko et al.

(10) Patent No.: US 6,464,842 B1
(45) Date of Patent: Oct. 15, 2002

(54) CONTROL OF SOLID STATE DIMENSIONAL FEATURES

(75) Inventors: Jene A. Golovchenko; Daniel Branton, both of Lexington; Derek M. Stein, Somerville, all of MA (US); Ciaran J. McMullan, Co Derry (IE); Jiali Li, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/599,137

(22) Filed: Jun. 22, 2000

Related U.S. Application Data

(60) Provisional application No. 60/140,021, filed on Jun. 22, 1999.

(51) Int. Cl.[7] .............................................. C23C 14/34

(52) U.S. Cl. ............................ 204/192.13; 204/192.11; 204/192.33; 204/192.34; 216/84; 216/59; 216/38; 216/96; 216/99; 427/8; 427/569; 427/578; 432/1; 73/866

(58) Field of Search ....................... 204/192.11, 192.13, 204/192.33, 192.34; 216/84, 59, 38, 96, 99; 427/8, 569, 578; 432/1; 73/866

(56) References Cited

U.S. PATENT DOCUMENTS

| | | | |
|---|---|---|---|
| 4,455,192 A | 6/1984 | Tamai | 156/628 |
| 4,728,591 A | 3/1988 | Clark et al. | 430/5 |
| 4,855,197 A | 8/1989 | Zapka et al. | 430/5 |

(List continued on next page.)

FOREIGN PATENT DOCUMENTS

| | | | |
|---|---|---|---|
| DE | 4433845 | 3/1996 | H01L/21/98 |
| EP | 0632494 | 1/1995 | H01L/21/66 |

OTHER PUBLICATIONS

Yoldas et al., "Formation of Broad Band Antireflective Coatings On Fused Silica For High Power Laser Applications," *Thin Solid Films*, vol. 129, pp. 1–14, 1985.

Shank et al., "Fabrication of high aspect ratio structures for microchannel plates," *J. Vac. Sci. Technol. B*, vol. 13, No. 6, pp. 2736–2740, Nov./Dec. 1995.

Gribov et al., "A new fabrication process for metallic point contacts," *Microelectronic Engineering*, vol. 35, pp. 317–320, 1997.

Desai et al., "Characterization of micromachined silicon membranes for immunoisolation and bioseparation applications," *Journal Of Membrane Science*, vol. 159, pp. 221–223, 1999.

(List continued on next page.)

*Primary Examiner*—Steven H. VerSteeg
(74) *Attorney, Agent, or Firm*—Theresa A. Lober

(57) ABSTRACT

There is provided controlled fabrication of a solid state structural feature on a solid state structure by exposing the structure to a fabrication process environment the conditions of which are selected to produce a prespecified feature in the structure. A physical detection species is directed toward a designated structure location during process environment exposure of the structure, and the detection species is detected in a trajectory from traversal of the designated structure location, to indicate changing physical dimensions of the prespecified feature. The fabrication process environment is then controlled in response to the physical species detection to fabricate the structural feature. Also provided is a method for controlling a physical dimension of a structural feature or to form a feature by exposing the structure to a flux of ions at a selected structure temperature, the exposure conditions being controlled to cause formation of the feature or to cause at least one physical dimension of the feature to be changed, substantially by transport of material of the structure to the structural feature in response to the ion flux exposure.

78 Claims, 18 Drawing Sheets

U.S. PATENT DOCUMENTS

| | | | |
|---|---|---|---|
| 5,244,527 A | 9/1993 | Aoyagi | 156/345 |
| 5,319,197 A | 6/1994 | Friedhelm | 250/305 |
| 5,420,067 A | 5/1995 | Hsu | 437/180 |
| 5,486,264 A | 1/1996 | Ghandour | 156/635.1 |
| 5,556,462 A | 9/1996 | Celii et al. | 117/85 |
| 5,753,014 A | 5/1998 | Van Rijn | 96/12 |
| 5,780,852 A | 7/1998 | Shu | 250/304 |
| 5,789,024 A | 8/1998 | Levy et al. | 427/244 |
| 5,798,042 A | 8/1998 | Chu et al. | 210/490 |
| 5,851,842 A | 12/1998 | Katsumata et al. | 438/9 |
| 5,868,947 A | 2/1999 | Sakaguchi et al. | 216/2 |
| 5,876,880 A | 3/1999 | Vonach et al. | 430/5 |
| 5,893,974 A | 4/1999 | Keller et al. | 210/483 |
| 5,962,081 A | 10/1999 | Ohman et al. | 427/534 |

OTHER PUBLICATIONS

Erlebacher et al., "Spontaneous Pattern Formation on Ion bombarded Si(001)," *Physical Review Letters*, vol. 82, No. 11, pp. 2330–2333, Mar. 1999.

Deshmukh et al., "Nanofabrication using a stencil mask," *Applied Physics Letters*, vol. 75, No. 11, pp. 1631–1633, Sep. 1999.

Wellock et al., "Giant magnetoresistance of magnetic multilayer point contacts," *Physical Review B*, vol. 60, No. 14, pp. 10292–10301, Oct. 1999.

Erlebacher et al., Nonlinear amplitude evolution during spontaneous patterning of ion–bombarded Si(001), *J. Vac. Sci. Technol. A*, vol. A, No. 18(1), pp. 115–120, Jan./Feb. 2000.

Closing Trenches

3 KeV, 20°C          3 KeV, 20°C

Opening Trenches

3 KeV, -100°C         3 KeV, -100°C

# CONTROL OF SOLID STATE DIMENSIONAL FEATURES

CROSS REFERENCE TO RELATED APPLICATION

This application claims the benefit of U.S. Provisional Application No. 60/140,021, filed Jun. 22, 1999, the entirety of which is hereby incorporated by reference.

This application is related to co-pending application entitled "Molecular and Atomic Scale Evaluation of Biopolymers," filed on even date herewith and incorporated by reference in its entirety.

STATEMENT REGARDING FEDERALLY SPONSORED RESEARCH

This invention was made with Government support under Contract No. N65236-99-1-5407, awarded by the Defense Advanced Research Project Agency. The Government has certain rights in the invention.

BACKGROUND OF THE INVENTION

This invention relates to fabrication of solid state structures, and more particularly relates to dimensional control of solid state structural features.

Precise dimensional control of solid state structural features is essential for many applications in fields ranging from biology and chemistry to physics, optics, and microelectronics. The term "solid state" is here meant to refer to non-biological materials generally. Frequently the successful fabrication of a solid state system critically depends on an ability to articulate specific structural features, often of miniature dimensions, within very tight tolerances. Accordingly, as solid state systems evolve to the microregime and further to the nano-regime, nanometric dimensional feature control is increasingly a primary concern for system feasibility.

There have been established a wide range of microfabrication techniques for producing and controlling structural feature dimensions in micromechanical and microelectromechanical systems. For example, high resolution lithographic techniques and high-precision additive and subtractive material processing techniques have been proposed to enable small-scale feature fabrication. But in the fabrication of many nano-regime systems, in which structural feature dimensions of a few nanometers are of importance, it is generally found that conventionally-proposed techniques often cannot form the requisite nano-scale features reproducibly or predictably, and often cannot be controlled on a time scale commensurate with production of such nano-scale features. As a result, volume manufacture of many systems that include nanometric feature dimensions and/or tolerances is not practical or economical.

SUMMARY OF THE INVENTION

The invention provides processes that enable reproducible and predictable production of structural features for solid state mechanical or electromechanical systems. The processes of the invention can be controlled to produce feature dimensions in the nano-regime and can include real time feedback control operating on a time scale commensurate with the formation of nano-scale solid state features.

In one technique provided by the invention, for controlled fabrication of a solid state structural feature, a solid state structure is provided and exposed to a fabrication process environment the conditions of which are selected to produce a prespecified feature in the structure. A physical detection species is directed toward a designated structure location during process environment exposure of the structure, and the detection species is detected in a trajectory from traversal of the designated structure location. This provides an indication of changing physical dimensions of the prespecified feature. The fabrication process environment is controlled in response to physical species detection to fabricate prespecified physical dimensions of the structural feature.

"Solid-state" is used herein to refer to materials that are not of biological origin. By biological origin is meant naturally occurring, i.e., isolated from a biological environment such as an organism or cell, or otherwise occurring in nature, or a synthetically manufactured version of a biologically available structure, or a synthetic or non-naturally occurring homologue or derivative of a naturally occurring material that substantially retains the desired biological traits of interest. Solid-state encompasses both organic and inorganic materials.

The structure can be provided as, e.g., a substrate of inorganic or material, or crystalline material, and can be provided as a semiconductor wafer, a membrane, a layer in which the prespecified feature is to be fabricated, or other suitable structure.

The fabrication process can be provided as, e.g., a sputtering environment such as ion beam or electron beam sputtering; as a wet chemical etch environment, such as an electrochemical etch environment; as a plasma environment; as a chemomechanical polishing environment; as an ion-induced or ion-assisted environment; as an environment for material deposition or growth; as a heating environment, or as another suitable environment.

In one example, the prespecified feature is an aperture, and the fabrication process conditions are selected to etch the aperture. Here the detection species trajectory can be through the aperture. An array of apertures can be formed in such a manner. The fabrication process conditions can be selected to enlarge or to reduce the aperture diameter.

Similarly, the prespecified feature can be a trench, a slot, or a gap between at least two structural edges, with the fabrication process conditions selected to enlarge or to reduce the trench, slot, or gap. The detection species trajectory can be through the trench, slot, or gap.

The detection species can be provided as atoms, ion, electrons, an etch species provided in the fabrication process environment, or other species. The species detection can be carried out by detecting the existence of the detection species in a trajectory from traversal of the designated structure location. The species detection further can be carried out by quantifying the detection species as a function of time. The fabrication process environment can be controlled by terminating exposure of the structure to the process environment at a point in time when the species detection indicates fabrication of prespecified dimensions of the structural feature.

This process can be applied, in accordance with the invention, to fabricate an aperture in a solid state structure. In this process, there is to be provided a solid state structure having a first surface and an opposing second surface. On the first structure surface is formed a cavity extending to a cavity bottom located at a point between the first and second structure surfaces. Then the structure is thinned from the second structure surface. A physical detection species is directed toward a location on the structure for the aperture as defined by the cavity, during the structure thinning, and the physical detection species is detected in a trajectory through the aperture when thinning of the structure causes the second structure surface to intersect with the cavity bottom. The structure thinning is controlled based on physical detection species detection.

This technique can be employed to produce an aperture of a prespecified diameter by quantifying the detected physical detection species during the structure thinning and then controlling the structure thinning based on the quantification to produce a prespecified aperture diameter.

The structure can be provided as a membrane, e.g., a silicon nitride membrane. The thinning can be carried out by any suitable process, e.g., sputtering. The detection species can be, e.g., ions or electrons, and the detection species can be distinct from a species employed for thinning the structure.

The invention also provides techniques for controlling a physical dimension of a solid state structural feature. In an example of such a process, a solid state structure having a structural feature is provided, and the structure is exposed to a flux of ions at a selected structure temperature. The exposure conditions are selected to cause at least one physical dimension of the feature to be changed substantially by transport of material of the structure to the structural feature in response to the ion flux exposure. Similarly, to fabricate a physical feature on the solid state structure, the structure is exposed to a flux of ions at a selected structure temperature. The exposure conditions are selected to produce a physical feature on the structure substantially by transport of material of the structure to the structural feature in response to the ion flux exposure.

The exposure condition control can include, e.g., control of structure temperature, control of ion flux, energy, species, or time structure, control of ambient gas species, or control of another suitable parameter of the exposure.

These processes can enable an increase or a decrease in feature dimensions, e.g., reduction in diameter of an aperture, reduction in a trench width, reduction in a gap width, or increase in a protrusion height. The structure can be provided as a crystalline substrate, a membrane, e.g., a silicon nitride membrane, or other structure. The ion flux can be provided as flux from a focused ion beam. In one example, a first membrane surface is exposed to ion flux to produce a protrusion on a second membrane surface opposite the first membrane surface. The physical species detection mechanisms described above can be employed to control ion flux exposure to change or produce a feature in a prespecified manner.

These processes enable fabrication of a wide range of structural features in a manner that is reproducible, controllable, and efficient. Applications in fields ranging from biology to microelectronics are enabled by these processes, and can be carried out in a manner that is commercially viable. Other features and advantages of the invention will be apparent from the following description and associated drawings, and from the claims.

DETAILED DESCRIPTION OF THE INVENTION

Figure 1A:
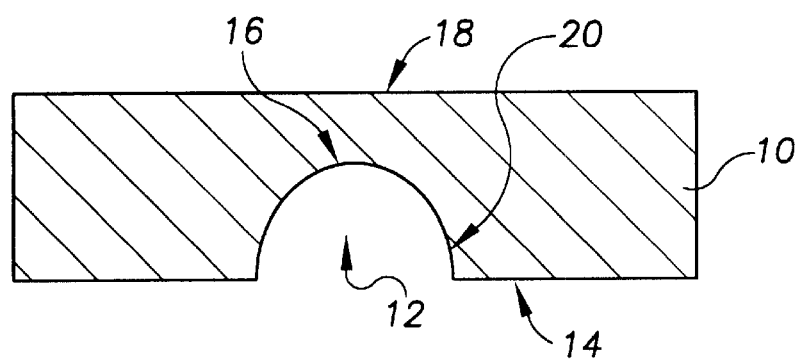
FIGS. 1A–1D are schematic cross-sectional views of fabrication sequence steps for the production of an aperture in accordance with the invention.

The processes for dimensional feature control provided by the invention can be directed to a wide range of materials and structural configurations. The example processes here described are meant to be illustrative but not to represent specific limitations in materials or configurations. The processes of the invention are particularly well-suited for precisely controlling structural feature dimensions, and for enabling such control on the scale of nanometers. This control can be especially advantageous for the precise formation and definition of nanometric-sized features and spaces, such as gaps existing as an aperture, e.g., pores, slits, orifices, vents, and holes, as well as trenches, channels, troughs, and in general, the spacing between two or more distinct feature edges.

Referring to FIG. 1, in one example implementation of a method provided by the invention for precisely and reproducibly defining the spacing of features, there is carried out a process for forming an aperture of a prespecified extent, e.g., diameter, in a structural layer. In a first process step, referring to FIG. 1A, a starting structure 10 is provided, shown in cross-section in the figure. Such starting structure 10 can be supplied as, e.g., a substrate, a thick or thin layer provided on a support such as a substrate, a membrane, or suitable structure. A cavity 12 is formed in the structure 10 on a selected surface 14 of the structure and in a region at which an aperture is desired.

The cavity 12 extends into the bulk of the structure 10 for only a fraction of the structure's thickness, rather than through the entire thickness of the structure, to an opposing surface 18. As a result, the deepest level, i.e., the bottom 16, of the formed cavity lies at some midpoint in the structure's bulk. As explained in more detail below, the geometry of the cavity bottom 16 and the cavity sidewalls 20 are preferably selected to enable controlled formation of a limiting aperture of controlled transverse and longitudinal dimensions in later processing steps. In the example illustrated, a bowl-shaped cavity is employed.

Figure 1B:
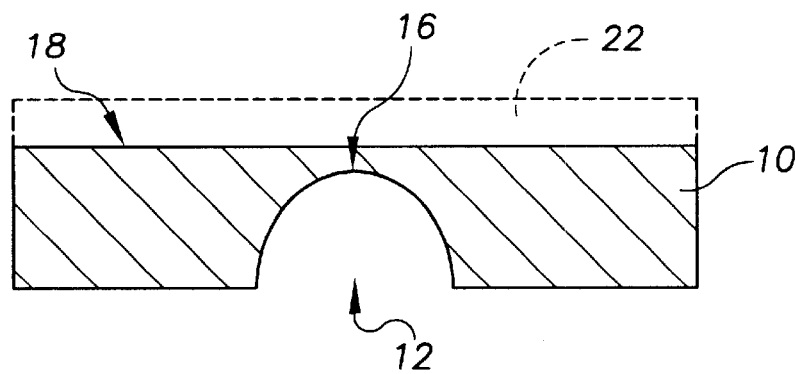
Figure 1C:
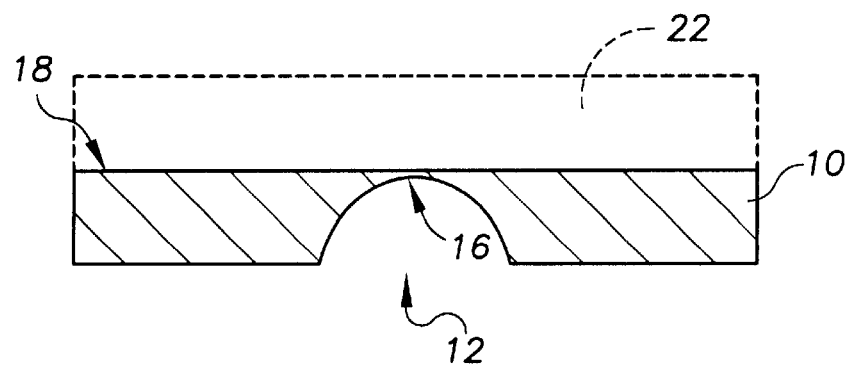

Referring to FIGS. 1B and 1C, once the cavity is produced, the structure is progressively thinned from the cavity-free surface 18. As the thinning is continued, a portion 22 of the structure is increasingly removed, shown by dotted lines. This causes the cavity-free surface 18 of the structure to advance toward the bottom 16 of the cavity.

Figure 1D:
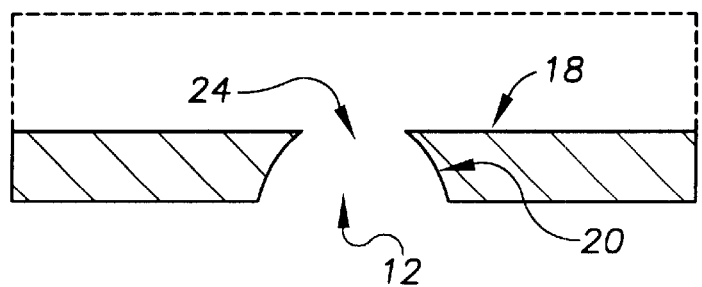

Continued thinning of the structure results in the intersection of the cavity-free surface 18 with the bottom 16 of the cavity, as shown in FIG. 1D. When this intersection occurs, a limiting aperture 24 is formed which transforms the cavity 12 to an aperture extending through the thickness of the structure. Further thinning of the structure causes the cavity-free surface 18 to intersect upper sidewall locations of the cavity, whereby the limiting aperture 24 takes on that profile of the sidewalls which exists at a given cavity intersection depth. In the example illustrated, the diameter of the limiting aperture 24 increases as thinning is continued, given the bowl shape of the cavity. It is to be recognized, however, that the diameter of the limiting aperture can be made to decrease as thinning is continued, for a corresponding cavity sidewall profile. In addition, asperities or other distinct profile features or geometry can be provided along the cavity sidewalls for controlling limiting aperture geometry.

This aperture forming process provides distinct advantages in that it does not rely on direct lithographic techniques for defining final limiting aperture and wall dimensions. As a result, the aperture forming process is not constrained by lithographic resolution limits. The process enables production of a limiting aperture dimension or diameter as small as 1–2 nanometers or less without the need for exotic or expensive processing apparatus.

As explained above, this aperture formation process can be carried out on any of a wide range of structures, such as substrates, layers, and films provided on a supporting structure or free-standing as, e.g., membranes. Solid state materials in general can be employed as the structural material in which an aperture is formed; microelectronic or semiconductor materials can be particularly effective in enabling efficient processing techniques, as described below. For example, the broad classes of inorganic and organic glassy materials, such as oxides, glasses, plastics, polymers, and organic films, e.g., PMMA, as well as crystalline materials, such as semiconductors, e.g., silicon and silicon nitride, and metals, as well as other materials can be employed. The invention is not limited to a particular structural material or class of structural materials. Preferably, the structural material is selected to meet the criteria of the application specified for the aperture.

The method is particularly well-suited for enabling formation of apertures in membranes, and for providing the nano-regime control of aperture formation that is required for many membrane applications. In the formation of a membrane aperture, microelectronic and semiconductor materials and fabrication processes can be advantageously exploited in accordance with the invention to enable cost-effective and efficient manufacturability.

Figure 2A:
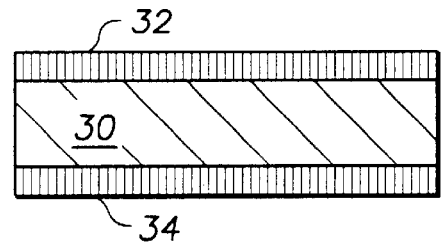
FIGS. 2A–2G are schematic cross-sectional views of an example fabrication sequence of steps for the production of the cavity of FIG. 1A in a membrane.

Referring to FIG. 2, in an example microfabrication process provided by the invention for forming an aperture in a membrane, a starting substrate 30, e.g., a silicon wafer, is provided, as shown in FIG. 2A. A selected membrane material, e.g., silicon nitride, is provided as a coating layer 32, 34 on the upper and lower surfaces, respectively, of the wafer. The thickness of the coating layer 34 is that thickness selected for the membrane to be formed. In one example, a silicon-rich, low-stress, silicon nitride layer of about 50 nm in thickness is deposited on the silicon wafer by conventional chemical vapor deposition (CVD) processing. It is recognized that additional membrane materials, e.g., silicon dioxide, can be deposited before or after deposition of the silicon nitride layers for mechanical stress control or other consideration. The silicon nitride layer can also be further processed, e.g., by ion implantation, to control mechanical membrane stress or adjust electrical or thermal conductivity of the membrane as desired for a given application.

Figure 2B:
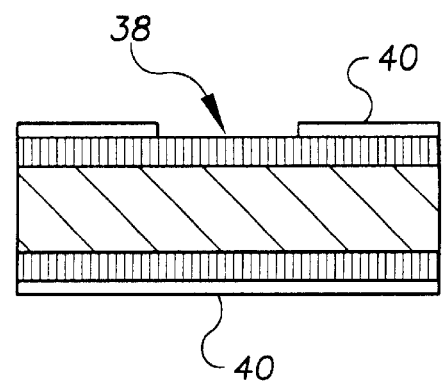
Figure 2C:
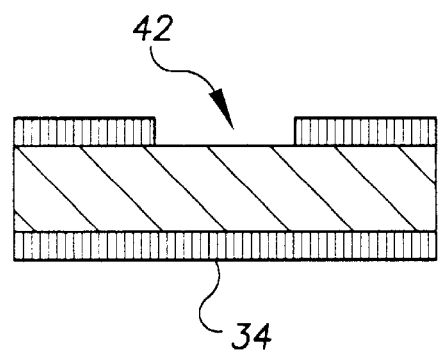

As shown in FIG. 2B, a layer of photoresist 40 is formed on one of the deposited nitride layers and patterned to define a nitride etch window 38. The opposing surface of the wafer is blanket coated with a photoresist layer 40. Then, as shown in FIG. 2C, the silicon nitride exposed by the nitride etch window 38 is removed by, e.g., conventional reactive ion etching techniques. This exposes a substrate etch window 42. The opposing nitride layer 34 is protected from this etch by the blanket photoresist layer 40, which is removed at the etch completion.

Figure 2D:
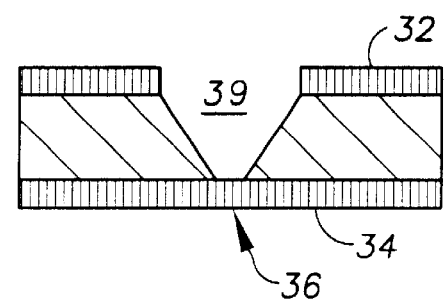

Next, referring to FIG. 2D, the silicon wafer is bulk micromachined by a suitable etch procedure, e.g., a conventional anisotropic wet etch process employing KOH. Preferably, the bulk wafer etch process employed is characterized by a high selectivity to the wafer material over the membrane material. In the example illustrated, the KOH etch substantially does not attack the silicon nitride layers. Continuation of the etch through the thickness of the wafer thereby produces a self-supporting nitride membrane 36 in a nitride layer 34. The nitride membrane forms the bottom of a pyramidal well 39 etched out of the silicon wafer due to the anisotropic, crystallographic-specific nature of the KOH etch. The extent of the nitride membrane is thus determined by the thickness and crystallographic orientation of the starting silicon wafer. As will be recognized, the membrane dimensions can therefore be controlled as-desired.

Figure 2E:
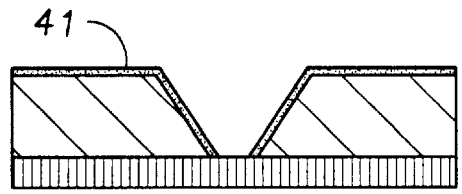

Referring to FIGS. 2D–2E, the remaining layer 32 of silicon nitride opposite the membrane layer can then removed if desired by, e.g., conventional reactive ion etching, and then a layer of silicon dioxide 41 is optionally grown on the exposed silicon surfaces, if electrical insulation of the silicon wafer is desired for a given application. Conventional wet or thermal oxide growth can be preferred over a CVD oxide layer such that oxide is only formed on the silicon surfaces in the manner illustrated. If, however, a composite membrane is desired, e.g., for mechanical stress control, then a CVD or other deposition process can be employed to produce an oxide layer on both the silicon wafer and the lower silicon nitride membrane surfaces, or on the nitride membrane surface alone.

Figure 2F:
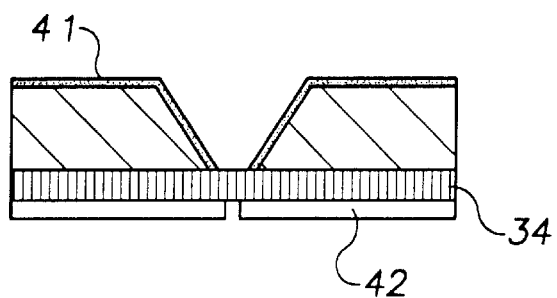

In a next step of the process, referring to FIG. 2F and referring back to FIG. 1A, a cavity is formed in a selected surface of the membrane. In one example cavity formation process, an etching process, as illustrated, a layer of resist 42 is formed on the lower membrane surface, i.e., the membrane surface opposite that in the pyramidal wafer well. The resist is then patterned to define the cavity to be formed in the membrane. This choice of surface for the cavity can be preferable for enabling a selected lithography technique on a flat surface; it can be difficult to effectively pattern a layer of photoresist provided on the membrane surface at the bottom of the silicon pyramidal well. If desired for a given application, however, the cavity can be formed on such a surface with lithographic techniques specific to such a configuration. The invention contemplates the use of photolithography, electron beam lithography, and other suitable lithographic processes for defining the cavity pattern. It is to be recognized that the selected lithographic process is preferably suited to the dimensions of the cavity; e.g., electron beam lithography can be preferred over conventional photolithography for cavities having submicron dimensions.

Figure 2G:
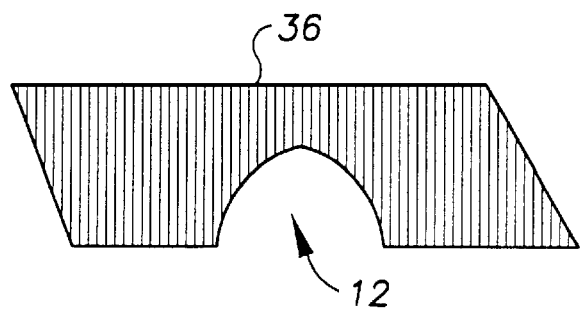

As explained above, the sidewall profile of the cavity to be formed in the membrane can be specified to produce a selected limiting aperture geometry. The lithographic step defining the cavity, as well as the nature of the cavity etch process itself, can also be employed to define the cavity sidewall profile. In one example scenario, the selected lithographic cavity pattern is continuous, e.g., as a circle, and a relatively isotropic etch process, e.g., an isotropic reactive ion etch process, is carried out to form a bowl-shaped cavity 12 in the nitride membrane 36, as shown in FIG. 2G. An isotropic reactive ion etch process inherently forms the bowl shape extending from a circular photolithographic pattern.

The invention contemplates the use of substantially any cavity pattern for achieving a desired cavity geometry. Square, rectangle, hexagonal, or other pattern, symmetric or asymmetric, can be employed. Due to the batch nature of lithographic processes and other microfabrication processes employed in the aperture forming method, arrays of cavities, of varying extent and geometry, can be defined in a single structure such as the membrane illustrated. Because the aperture formation process of the invention relies on structural thinning, rather than lithography, to define the final limiting aperture geometry, the largest lateral dimension of the cavity can be much greater than the desired limiting aperture extent; in general, the largest cavity pattern dimension can be two or more orders of magnitude larger than a selected limiting aperture diameter. Preferably, given the characteristics of a selected cavity etch process, the cavity pattern extent is correspondingly selected to produce a desired extent at the cavity bottom, and to produce a range of cavity expanses between the cavity bottom and the material surface.

Any suitable cavity etch process can be employed, including, e.g., plasma etching, focused reactive ion etching, focused ion beam etching, wet chemical etching, or other selected technique. Whatever etch process is selected, it is to be controlled to enable termination of the etch at a cavity bottom located at some distance within the membrane thickness or other structure in which the cavity is formed, i.e., at a point between the surfaces of the structure. For etch processes that are fully characterized for the structural material being employed, this can be accomplished by a timed etch; conventional diagnostic techniques otherwise can be employed in the conventional manner to produce a cavity bottom at a selected location in a membrane other structure. It is not required in accordance with the invention to precisely position the cavity bottom at a known, a priori depth in the structure. The progressive structural thinning process of the invention is particularly advantageous in this regard; no precise control or knowledge of the depth of the cavity is required to precisely produce an aperture. In addition, a combination of etch processes can be employed as-necessary for cavity formation in a given material or composite of materials. For example, where a composite membrane is formed of silicon nitride and silicon dioxide layers, the chemistry of a selected cavity etch, such as a plasma etch, can be adjusted over the course of the etch based on the material to be etched at a given time in formation of the cavity. Similarly, a combination of etch processes can be employed to alter the cavity sidewall profile as a function of cavity depth. For example, a combination of isotropic and anisotropic wet etches can be employed to produce selected curvature and slant of cavity sidewalls formed in a nitride or silicon layer or membrane. A combination etch such as this enables the formation of asperities or other distinct features to be located at the limiting aperture.

Referring back to FIGS. 1B–1D, once a cavity has been formed in the selected membrane or other structure, thinning of the structure is then carried out on the structure surface opposite that in which the cavity was formed, employing an appropriate procedure to open a limiting aperture in the structure. The invention contemplates a wide range of thinning processes and is not limited to a particular thinning technique; all that is required is the ability to etch back the structure from a surface opposing that in which the cavity was formed.

For many applications, a particularly well-suited thinning process is ion beam sputtering. In such a process, a beam of ions is directed to the structure surface to be thinned to sputter etch away material from that surface. In typical ion beam sputtering processes at relatively low beam energies, e.g., in the range of keV, for every incident ion, on average, a single atom of material is ejected from the sputtering target; sputtering may thus be considered as an atomic-scale version of "sand blasting." In the case of, e.g., a silicon nitride membrane, such sputter etching results in the removal of about one atomic layer of silicon nitride from the membrane per second for incident ion fluxes between about $10^{14}$–$10^{15}$ ions/cm$^2$/sec. When the surface exposed to the sputtering beam has been sufficiently thinned that the surface intersects with the cavity bottom, a limiting aperture is formed.

The invention contemplates a wide range of additional thinning processes, including ion beam assisted etching, ion beam induced etching, electron beam etching or assisted etching, plasma and reactive ion etching, wet etching such as electrochemical etching, chemomechanical polishing, and other fabrication and manufacturing processes that enable controlled thinning of a structure to intersect a cavity on a surface opposite that being thinned. These aperture formation processes can be advantageous for many applications because during the thinning etch, the etch species, e.g., a sputtering ion beam or reactive plasma environment, need not be focused on a particular location of the structure surface being thinned. A blanket exposure of the structure surface can be employed to thin the entire extent of the structure. All that is required is that the structure surface including the cavity be isolated, i.e., shielded, from the etch species attacking the opposing surface. This results in nano-regime precision in feature formation without the requirement of nano-regime control of the etch apparatus and species.

Whatever thinning process is selected, the inventors herein have discovered that highly precise aperture formation can be accomplished by implementing a feedback mechanism during the thinning process. This feedback mechanism is based on detection of a physical species provided during the thinning etch in a manner that is indicative of the physical dimensions of a feature, e.g., an aperture, that is being produced by the etch. Such feedback enables real time control of the aperture formation process, whereby a precise and prespecified aperture diameter can be reliably and reproducibly formed. As explained later in the description, this feedback mechanism can in general enable precise sculpting of nanometric features and nanostructures, and finds wide application for micro- and nano-systems.

Considering feedback control in the aperture formation process of the invention more specifically, when an etch species, such as a beam of sputtering ions, thins a structure to the point that an aperture is formed, ions from the beam are at that point in time enabled to pass through the aperture. Thereafter, the number of ions passing through the aperture per unit time is proportionally related to the increasing diameter of the aperture as the thinning etch continues. Detection and quantification, e.g., by counting, of the rate and/or number of ions passing through the aperture thereby is indicative of the aperture diameter at any given time during the etch.

As a result, a selected aperture diameter can be prespecified based on a rate and/or number of ions expected to pass through the aperture before the selected diameter is produced. During a thinning etch process, a first passage of ions through a newly-formed limiting aperture can be detected, and the number of ions passing through the aperture as its limiting aperture dimension enlarges can be individually detected and quantified. When the prescribed number of ions pass through the aperture, a controlling signal can be sent to the sputtering ion beam controller to terminate the etch process at the desired aperture dimension. In addition, it is recognized in accordance with the invention that detection of a physical species can be carried even prior to the time at which an aperture is formed. For example, the level of X-rays produced by the ion beam gun that are detected as passing through the structure being thinned can be expected to increase as the thickness of the structure decreases. Detection of ions similarly can be made even prior to aperture opening. This enables control of the process even prior to the final opening of the aperture.

Figure 3A:
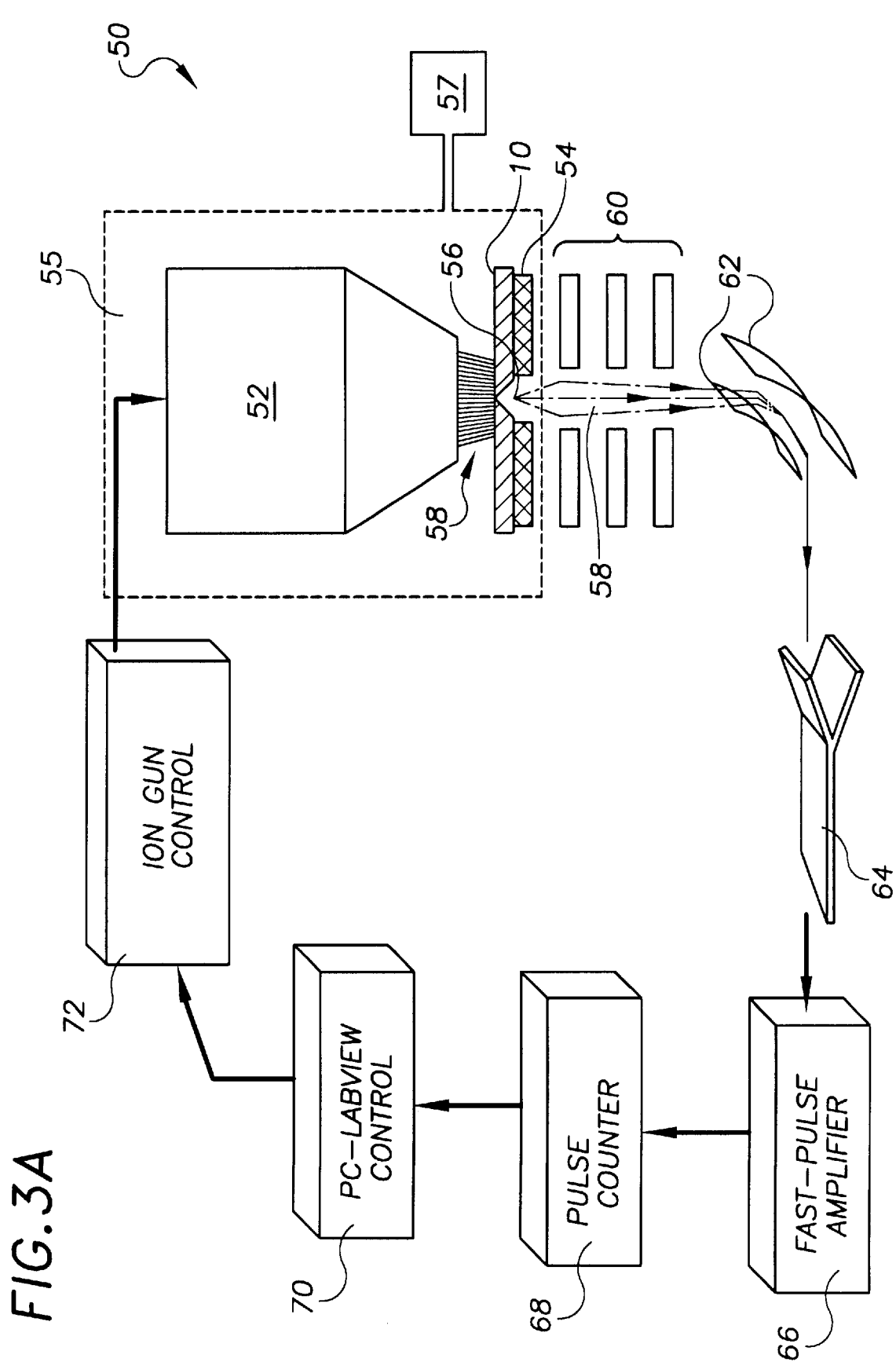
FIGS. 3A–3B are schematic diagrams of an ion beam sputtering system configured in accordance with the invention to implement precision feedback control.
Figure 3B:
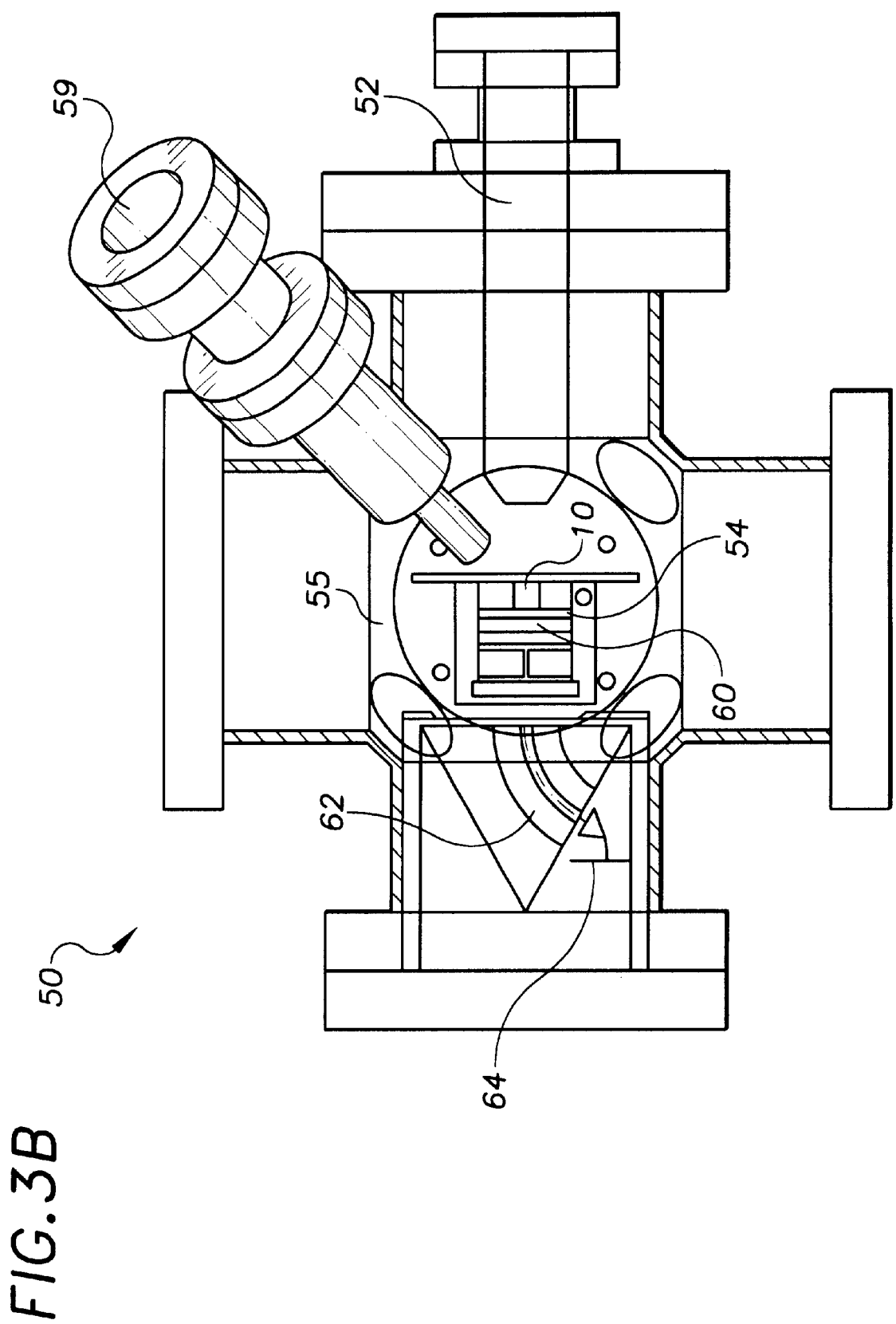

Referring to FIGS. 3A–3B there is schematically shown a system 50 for implementing this feedback-controlled sputtering process. The system includes an ion gun 52, e.g., an ion gun capable of producing an ion beam with an energy range and diameter suitable for a given application. In general, an energy between about 1 eV and about several hundred KeV and a beam diameter between about a few nanometers to spatially very broad beams can be employed. A vacuum etch chamber 55 is provided in which the etch process can be carried out. Preferably, the etch chamber pressure is well-controlled such that etch environment pressures of less than about $10^{-8}$ Torr can be maintained during the etch process. A turbomolecular pump 57 is provided for pressure control and maintenance. Optionally, a mass spectrometer can be provided for monitor and analysis of the etch environment species.

A structure holder 54 is provided for supporting a structure 10 in which an aperture is to be formed, e.g., employing clips to maintain the position of the structure. Preferably, the holder 54 is thermally conductive and provides structure temperature control, e.g., by a liquid heat exchange loop, employing a thermocouple positioned on the holder or on the structure itself. For many applications, it can be preferable that the holder also be electrically conductive to enable voltage charge control of the structure and to enable monitor of incident ion beam current.

The holder includes a central aperture 56 corresponding to the location at which an aperture is to be formed in the structure 10. With this configuration, a beam of ions 58 directed from the ion gun toward the structure 10 thins the structure to form therein an aperture, after which time the ion beam 58 traverses both the structure aperture and the holder aperture.

Referring to FIG. 3B, an electron flood gun 59 can be included in the arrangement to direct a beam of electrons at the structure being etched during the etch process. For structures such as a silicon nitride membrane that are electrically insulating, positive electrical surface charge can accumulate on the structure due to positively-charged ion beam irradiation. Electron beam irradiation of the structure can be carried out to neutralize this surface charge, if necessary for a given application.

If the thinning etch process is to be controlled by a feedback mechanism in accordance with the invention, then the stream of a species traversing the etched aperture is to be detected and quantified in the manner described below. If no such feedback control is desired for a given application, then no additional apparatus is necessary, and the sputtering can be carried out in a conventional sputtering chamber under conditions selected for a given etch.

In accordance with the invention, species detection and quantification systems can be included to provide a desired degree of feedback control. Given a scenario where the selected sputtering beam ions employed for the thinning etch are electrically charged, ion focusing optics 60 can be provided for focusing the ions once they traverse the aperture, to facilitate ion detection by a detector that is relatively distant from the structure aperture through which the ions traversed. X-Y deflection optics and Einzel lenses can be employed in conventional configurations to produce a desired focusing of the ions. In the conventional manner, optics design software can be employed to produce a customized focusing configuration for a given detection arrangement. It is to be recognized that such focusing configuration may not be required for configurations where the ion detection system is relatively near to the holder aperture.

If employed, the focusing configuration preferably directs the output ion beam to an ion energy analyzer 62 for filtering the beam for the selected species to be detected and quantified by, e.g., counting. In general, it can be expected that the ion beam sputtering process will include and produce a wide range of physical species and radiation, including, e.g., sputtered silicon nitride atoms, etch species scattering in the etch chamber, and X-rays emanating from the ion gun. To enable highly precise etch control, the species to be detected is preferably filtered out from the produced radiation, produced etch species, and background radiation. Such background can be minimized by, e.g., isolating the ion beam gun, the structure to be etched, and the downstream optics from further downstream components such as detectors, as described below, by an electrostatic energy filter or other suitable filter. In addition, it can be preferable to maintain the ion beam gun, structure, and optics at reduced temperature conditions in a suitable vessel, as shown in FIG. 3B, whereby thermal effects can be controlled. Such a cooling configuration is also useful to maximize cleanliness of the etch and beam detection environment and to control structure temperature. It can also be advantageous to maintain the structure at an elevated temperature to influence materials modification phenomena during ion irradiation.

The employment of an ion energy analyzer 62 or other species-specific filtering system is advantageous in that it enables redirection of a species to be detected out of the line of sight of the sputtering trajectory. The species detection location can then be distant and out of line from bombardment by background and produced radiation such as X-rays. For example, as shown in FIGS. 3A–3B, the electrostatic energy analyzer employed produces a 90° bend in the trajectory of the ion species to be detected, whereby that species is separated from the other species and radiation coming from the etched structure. If the detection resolution and speed desired for a given etch process do not require a low background noise environment, then the ion energy analyzer is not required for many applications.

The filtered species of interest output from the electrostatic energy analyzer is directed to a detector 64. For the detection of an electrically charged ion species, it can be preferable to employ a high-resolution, single ion detector, e.g., a Channeltron 4860 detector from Gallileo Electro-Optics of Sturbridge, Ma. Such a detector can be configured to produce one electrical output pulse per detected ion. Such single ion detection and associated counting can be preferred for many applications to enable nanometric-scale precision in production of a solid state feature such as an aperture. While a typical sputtering beam current density is about 10 ions/$nm^2$/sec, etching of a nanometer-range aperture requires counting of the passage of no more than about 10–20 ions through the aperture. Thus, a single ion detection and counting system, or another system of equivalent resolution, is preferred to reproducibly implement nano-regime control of feature production. If the features to be produced for a given application do not require nanometric dimensional control, then a more coarse detection mechanism can be employed.

Given a single ion detector configuration, a fast pulse amplifier 66 can be employed to modify the electrical output of the detector to facilitate an ion counting process. A suitable pulse preamplifier can be constructed in a conventional manner or a suitable commercial system, e.g., the VT120 Fast Preamp from EG&G Ortec of Oak Ridge, Tenn., can be employed. In one example scenario, given the production of a 10 mV ion detection pulse by the ion detector, the pulse amplifier 66 can be configured to amplify the pulse voltage to about 1 V. This amplified detection pulse is directed to a counting system, e.g., a universal counter such as the HF53131A by Hewlett Packard, for producing an electrical signal indicative of the number of detected ions. It is recognized that detection pulse amplification may not be required for a given pulse counter configuration, and that the pulse amplification, if implemented, is preferably controlled based on requirements of the counting system.

The electrical output of the pulse counter 68 is directed to a controller 70 that implements, e.g., monitor and control software for enabling an operator to monitor the thinning etch process in real time and for producing an ion gun control signal. In one example, the controller is implemented in software employing, e.g., Labview, from national Instruments of Austin Tex. Whatever controller implementation is selected, it preferably provides ion beam control signals based on the ion feedback. For example, the controller can be implemented to initiate ion beam sputtering of the structure for a specified time interval and to configure the counter to count the number of ions received at the detector during the specified time interval. At the end of the interval, the number of ions counted is determined by the controller and the extent of the aperture can at that point be calculated based on this ion count and the known ion flux. The number of ions counted during the interval is then employed by the controller to determine if a further interval of ion beam sputtering is to be initiated to continue etch of the structure.

In one advantageous configuration, a computer system including monitor, memory, and associated input/output and printing systems is provided for enabling visual monitoring and recording of the etch process progression. Display of the ion count rate and aperture extent over time, and storage of count rate and other system values can be preferable for many applications.

The output of the controller 70 is directed to an ion gun control system 72 for controlling the sputtering etch itself. In one example implementation, ion gun feedback control is effected by control of the ion gun's X-Y deflection plates to deflect the ion beam away from the structure 10 at the time when the desired aperture dimension is produced. This can be a preferable control technique because of the rapid speed at which the beam can be deflected, typically in much less than a millisecond. It is recognized, however, that alternative beam control mechanisms can be employed. For example, an electrostatic grid can be located between the gun and the structure holder. In this scenario, the grid is energized in response to an ion beam termination control signal to return the beam back toward the ion gun. In a further technique, the accelerating electron impact voltage of the ion gun can be controlled in response to an ion beam termination control signal to terminate production of the ion beam. These techniques are advantageous in that they suppress all sputtering after the desired aperture dimension is produced, whereby possible contamination of the sample is eliminated.

With a sputtering system and feedback/control hardware configuration in place, a feedback calibration curve can be produced for a given ion beam species, structure material, and aperture geometry to be produced. Such a calibration curve enables specification of the relationship between ion count number and/or rate and limiting aperture dimension, and can be established empirically, to specify for a particular structural material and thickness a relation between number of measured counts per time and actual limiting aperture dimension.

It is found that for many configurations, the relationship between limiting aperture dimension and ion count is generally linear. For this and other generally-predictable relationships, an extrapolated calibration curve can be produced based on a few measurements. To produce each such measurement, a thinning etch is carried out for a prescribed duration, during which an ion count is made and at the end of which an aperture dimension is physically measured by, e.g., transmission electron microscopy. Multiple etch durations and dimensional measurements can be carried out on a single aperture as that aperture is increased from etch to etch. A calibration curve can then be produced based on the ion count and aperture measurements and extrapolated to lower and higher ion counts. With such a calibration curve in hand, the controller system of the feedback configuration can be programmed to direct a controlling etch termination signal to the ion gun when the prescribed ion count corresponding to a desired aperture dimension is reached.

It is to be recognized that etch environment temperature and pressure, mechanical stress and temperature of the structure being etched, and feature dimensions and structural aspects can influence the relationship between detected ion count rate and physical feature dimensions. For example, the residual mechanical stress in a silicon nitride membrane can impact its etch characteristics. Similarly, the density of apertures in an array to be formed, the aperture proximity to each other, and other aspects can impact etch characteristics. It is therefore to be recognized that the calibration curve preferably is produced with consideration for various physical and etch environment parameters that can impact etch characteristics.

EXAMPLE 1

Figure 4A:
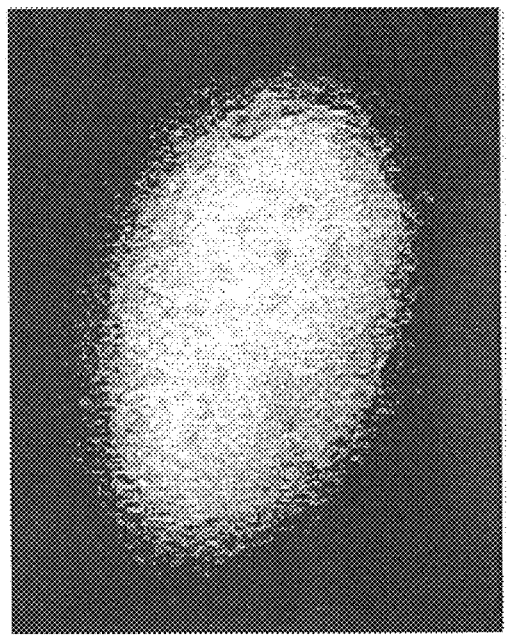
FIG. 4A is an electron micrograph of a cavity formed in a 500 nm-thick silicon nitride membrane in accordance with the invention.

A 50 nm-thick silicon nitride membrane having a cavity formed on one surface was produced by the process outlined in FIGS. 2A–G. The silicon nitride was deposited by low pressure chemical vapor deposition. The cavity bowl was etched in the membrane by a reactive ion etch process. FIG. 4A is an electron micrograph of the cavity formed in the membrane.

The membrane surface opposite that including the cavity was exposed to an argon ion beam etch at an energy of about 3 KeV, and a flux of about 3 $Ar^+sec/nm^2$. The ion beam diameter was about 200 $\mu$m and the membrane temperature during the etch was maintained at about −120° C. The ion beam was directed toward the membrane for 1 sec during each 5 sec interval. During the etch process, ion detection and counting was carried out.

Figure 4B:
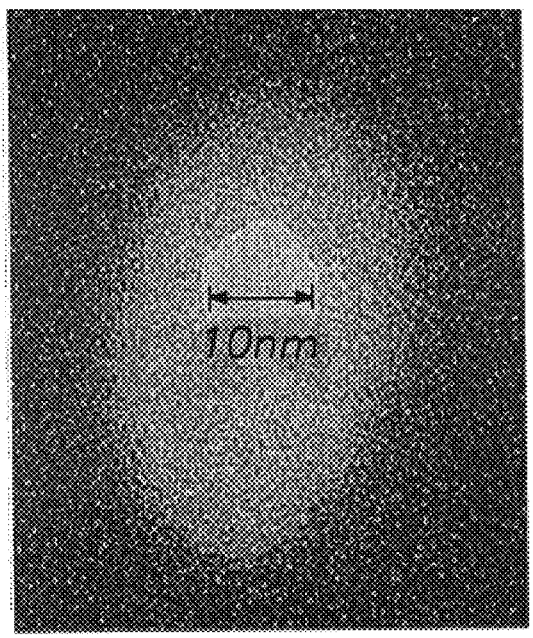
FIG. 4B is an electron micrograph of a 10 nm-wide aperture formed in a silicon nitride membrane by a process provided by the invention.
Figure 4C:
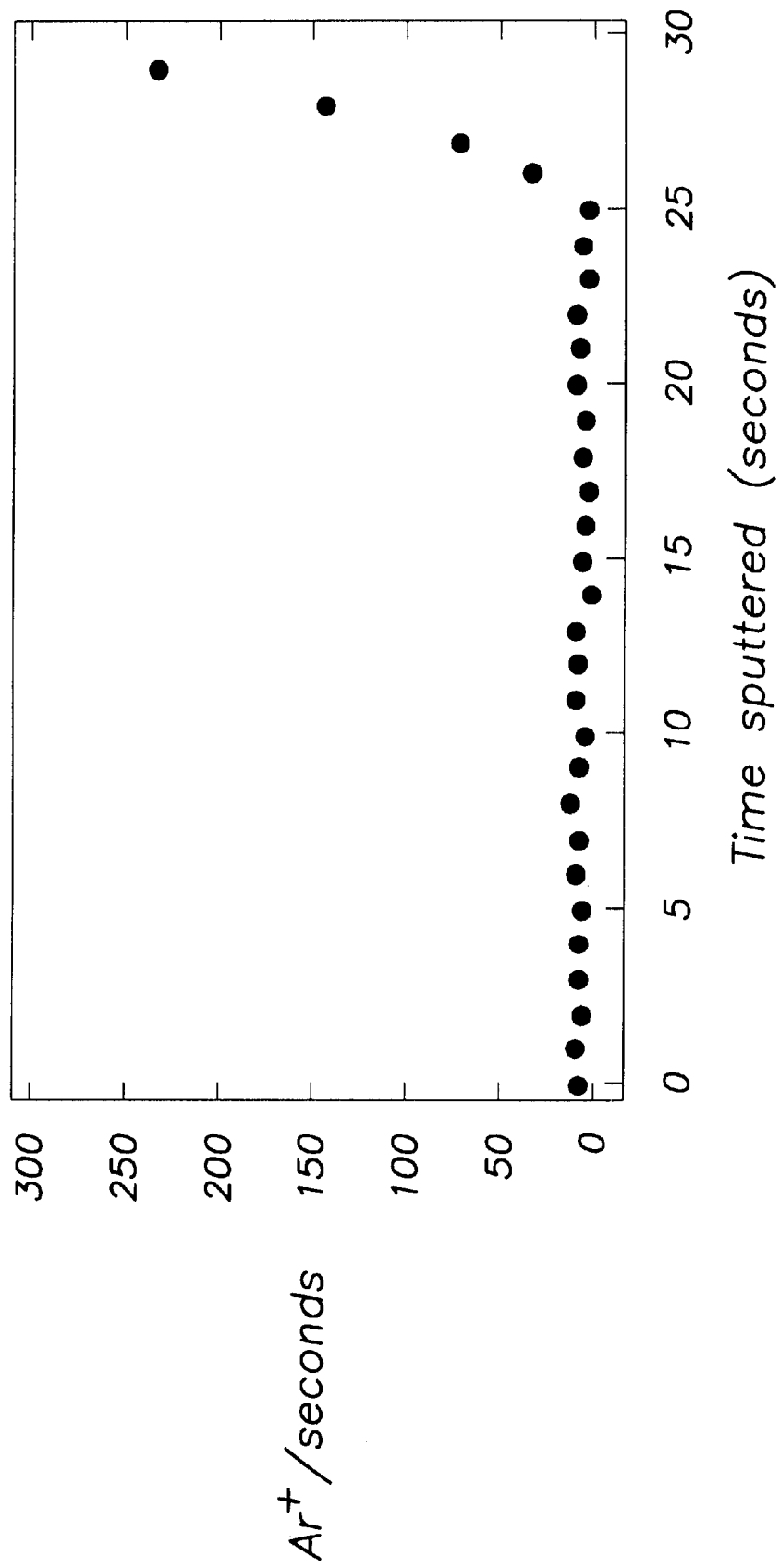
FIG. 4C is a plot of detected ion counts as a function of time for the aperture etch process that resulted in the aperture shown in FIG. 4B.

FIG. 4B is an electron micrograph of the membrane cavity including a 10 nm limiting aperture formed by thinning of the membrane. FIG. 4C is a plot of argon ion count/second as a function of sputtering time. This plot includes that time when the ion beam was directed to the membrane, not when the beam was deflected away from the membrane. As indicated by the plot, the number of counted ions/sec was substantially zero until at point in time, at 25 sec, when the limiting aperture was opened. Then as the limiting aperture diameter increased, the ion counts correspondingly increased. This enables control of the aperture formation process.

In this example, precise and controlled etch of the aperture was enabled by detection and counting of electrically charged ions that traversed the aperture once it was opened. Here the species operating as an etchant also operated as the species to be detected. In accordance with the invention, this dual role of the ion beam is not in general required. In an alternative scenario provided by the invention, the etchant species is selected and operates distinctly from the detection species. For many applications, such a decoupling of the etchant and detection species can be advantageous in enabling a broader range of candidate species for both etchant and detection species.

Considering an atom beam etch species, if the beam is electrically neutral rather than electrically charged, detection of the atoms can be difficult. A distinct non etching detection species such as an electron beam can in this case advantageously be employed for controlling formation of a prespecified aperture diameter. Such a scenario can be preferable where the structure being etched may become electrically charged by the impinging sputter beam, thereby warranting the use of an electrically neutral beam. For many applications, it can be preferable to employ an electrically charged detection species, for facilitating beam bending, filtering, and detection and counting with conventional techniques. Electrically neutral detection species can be employed, however, when such is optimal for a given application. For example, laser fluorescence of electrically neutral transmitted atoms can be employed for detecting and counting control functions.

When employed, a separate detection species is preferably one that can be directed in some manner toward a feature being produced and whose movement in the vicinity of the feature is indicative of changing dimensions of the feature. This enables detection of the species in a manner that is indicative of changes in the feature's dimensions. For example, in the case of formation of a membrane aperture, direction of an electron beam toward the membrane, such that electrons traverse the membrane aperture once it is formed, enables counting of electrons in the manner of ion counting described above. The invention does not require the use of a single detection species; more than one detection species can be employed. For example, X-rays produced by the ion gun can be monitored as the structure thins to predict and indicate a the time of a further aperture formation event. Thereafter, ions, electrons, or other species can be employed to monitor changes in aperture diameter. Neutral species and other species suited to a given application can similarly be employed together to provide precise detection and feedback mechanisms.

In addition, the invention does not require that the detection species be directed orthogonally to the plane of a feature being produced. For example, electron beam diffraction detection and the diffraction patterns produced by a material can be employed as a feedback mechanism. In such a case, e.g., where a feature in an upper layer is formed by removal of the upper layer to expose a lower layer or substrate, detection of the electron beam diffraction pattern characteristic of the lower layer can be employed as the feedback mechanism. Here the electron beam makes a glancing angle with the material. Similarly, in the case of formation of, e.g., an aperture, diffraction can be detected as a function of the aperture diameter by diffraction rings indicative of changes in aperture periphery. The diffraction feedback mechanism here occurs at the aperture periphery rather than as a trajectory through the aperture.

In a further example, an electron beam can be directed parallel to the upper structure surface being thinned in formation of an aperture, whereby the withdrawal of surface material is indicated by an increase in electron count in a direction parallel to that surface.

The invention contemplates alternative detection species. For example, atoms in a meta-stable state, e.g., an electronic meta-stable state, can be directed toward a feature being formed and detected once past the feature. Such meta-stable atoms, e.g., excited states of helium or argon, are electrically neutral and do not decay until hitting a solid surface, at which time an electron is liberated and can be detected and counted. Whatever detection species is selected, it preferably is one that can be detected and counted on a time scale that is commensurate with the desired dimensional scale of control in the feature being produced. For example, where nanometric feature dimensions are of importance, microsecond detection and counting processes are preferable to enable high sensitivity and resolution in the feedback mechanism. Less strict sensitivity and resolution requirements need be placed on detection species for micro- and macro-scale feature control.

The invention contemplates application of physical species detection and counting for feedback control in a wide range of fabrication processes. Many fabrication processes that are conventionally carried out in open loop fashion, i.e., without feedback control, can be adapted to enable nanoscale dimensional feature control with the incorporation of the highly sensitive and precise feedback mechanisms provided by the invention. For example, in the aperture formation process described above, reactive ion etching in a plasma, rather than sputter etching, can be employed to thin a structure surface in formation of a limiting aperture. In such a plasma etch process, the structure surface including a cavity is isolated from the plasma environment by a suitable fixture. The opposing structure surface is fully exposed to the plasma environment. As the plasma etch progresses to thin the structure and eventually produce a limiting aperture and growing aperture, ions traversing the aperture are detected by, e.g., a channeltron positioned on the isolated side of the structure. Accordingly, in the manner of the ion sputtering etch described above, feedback control can be imposed on the plasma etch process based on the detection and counting of plasma ions traversing the aperture.

In a further example process contemplated by the invention, physical detection and feedback control can be imposed on a wet etch process employed to produce a feature. For example, in formation of an aperture in a structure, electrodes can be provided near to the cavity formed in the structure. Here the structure surface opposite the cavity is exposed to a wet etch environment, e.g., an electrochemical environment, and the structural surface which includes the cavity is isolated from the etch environment. As the wet etch progresses to thin the structure and open an aperture, ions in the liquid that traverses the aperture can be detected and counted at the cavity-side electrodes. This enables feedback control for terminating the electrical stimulus of the etch at a time when the desired aperture dimension is attained.

The invention contemplates implementation of physical species detection and feedback process control for enabling fabrication of a wide range of structural, solid state features. The feedback mechanism is not limited to the aperture formation process described above. As explained above, an aperture, slit, trench, hole, or gap between two feature edges can be precisely formed, by any of a wide range of processes, in a precise and controllable manner with the feedback mechanisms of the invention.

For example, in a membrane aperture formation process employing, e.g., focused ion beam or plasma etching techniques where a hole is formed directly through the thickness of the membrane from one surface to the other of the membrane, feedback can be employed to control and monitor the formation. Similarly, the invention contemplates a membrane aperture formation process where a cavity is formed in one surface of the membrane and then that membrane surface, including the cavity, is exposed to, e.g., an ion sputtering etch. Because the thickness of the membrane between the cavity bottom and the opposing surface is much less than at other membrane regions, such etching opens a limiting aperture at the base of the cavity before completely etching away other regions of the membrane. The feedback mechanisms of the invention enable precise control and monitoring of this process.

EXAMPLE 2

Figure 5A:
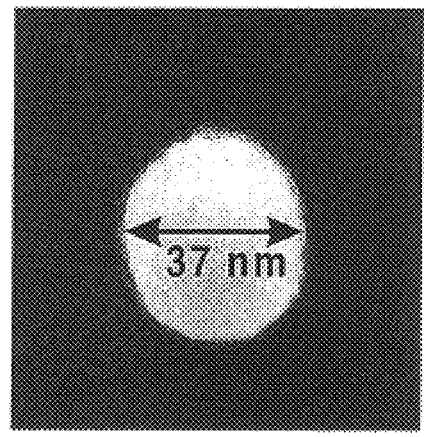
FIG. 5A is an electron micrograph of a 37 nm-wide aperture formed in a 500 nm-thick silicon nitride membrane in accordance with the invention.

A silicon nitride membrane of about 50 nm in thickness was produced in the manner of FIGS. 2A–2E. An aperture was formed through the entire thickness of the membrane by reactive ion etch. This resulted in a 37 nm-wide aperture, an electron micrograph of which is shown in FIG. 5A. The membrane and aperture were then exposed to an argon ion beam at a flux of about 1.7 $Ar^+/nm^2/sec$ and an energy of about 3 KeV. The ion beam was directed toward and away from the membrane to sputter for 1 second during each 5 second interval. The membrane was maintained at a temperature of about −102° C. during the ion beam exposure.

Figure 5B:
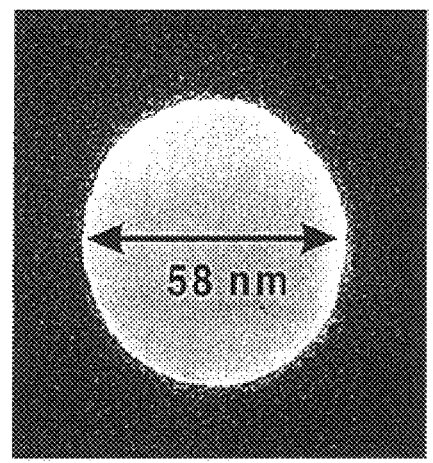
FIG. 5B is an electron micrograph of the aperture of FIG. 5A enlarged to 58 nm in width by a process provided by the invention.
Figure 5C:
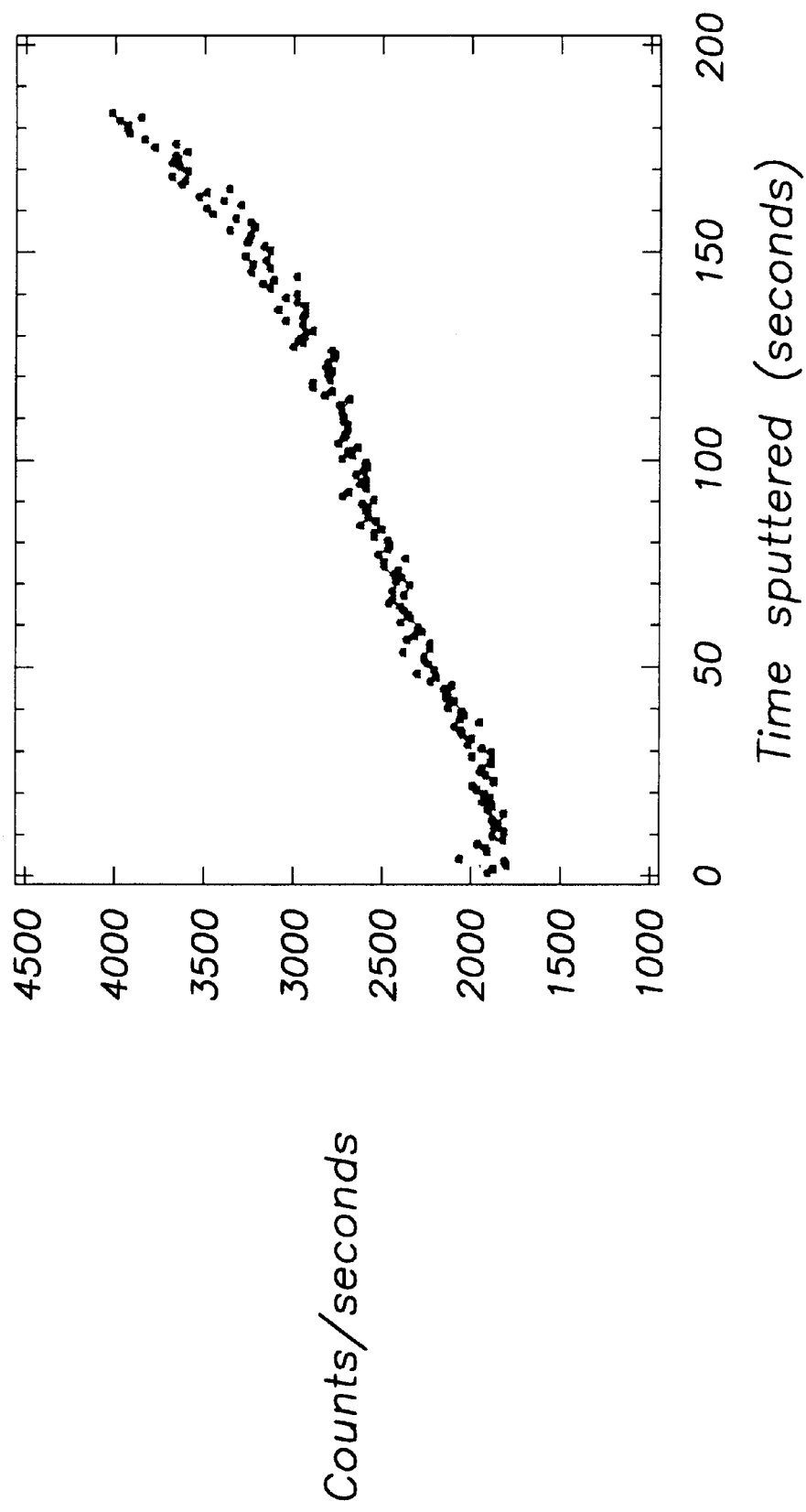
FIG. 5C is a plot of detected ion counts as a function of time for the aperture etch process that resulted in the aperture increase from that shown in FIG. 5A to that shown in FIG. 5B.

FIG. 5B is an electron micrograph of the 58 nm-wide aperture that resulted from 180 seconds of sputtering. FIG. 5C is a plot of counted ions/sec as a function of time. A generally linear relationship between ion counts as a function of time is demonstrated.

The invention does not require that the process being controlled by feedback be a subtractive process as in Example 2; additive processes can also be controlled by the feedback techniques of the invention. For example, an aperture, trench, or hole of a given dimension can be diminished or narrowed, by a suitable process, during which the physical species detection and feedback process control of the invention is imposed to control the diminishing process.

Sintering, heating, material deposition, material growth, and other suitable processes are contemplated as being controllable by the feedback mechanism of the invention. Similarly, oxidation, swelling, material flow and transport as described in detail below, condensation, evaporation, electroplating, ion- or electron-assisted deposition or growth, and other such additive processes can be controlled in accordance with the invention. The only requirement of the process to be controlled, whether additive or subtractive, is that the process accommodate the introduction of some detection species near to the structural feature being processed in a manner that enables detection of that species as an indicator of changing feature dimensions. As explained above, the features can be produced in a membrane, in a layer or layers provided on a support structure, or in a structure itself, e.g., a silicon wafer. Whether the process being controlled is additive or subtractive in nature, the advantages of the control processes of the invention can be most fully exploited and realized in the formation of nanometric scale feature dimensions and dimensional tolerances.

This capability can be particularly advantageous for producing a field of nanometric features, e.g., in formation of a lithographic mask plate. Here, e.g., a starting membrane can be processed with selected geometries to ultimately form wires, pads, and other mask plate geometries by additive or subtractive processes. This enables precise formation of the mask plate features in an efficient and effective process.

In another aspect of the invention, the inventors herein have discovered that the conditions of interaction between an ion beam and a solid can be controlled for manipulating nanoscale feature dimensions in solid state materials. These controlled ion beam interaction techniques enable solid state material topology to be adjusted, rather than necessarily removed. Specifically, under selected process conditions provided by the invention, solid state material can be caused to transform such that feature edge locations are precisely and controllably produced and/or modified by atomic transport mechanisms that are locally additive or subtractive.

Figure 6A:
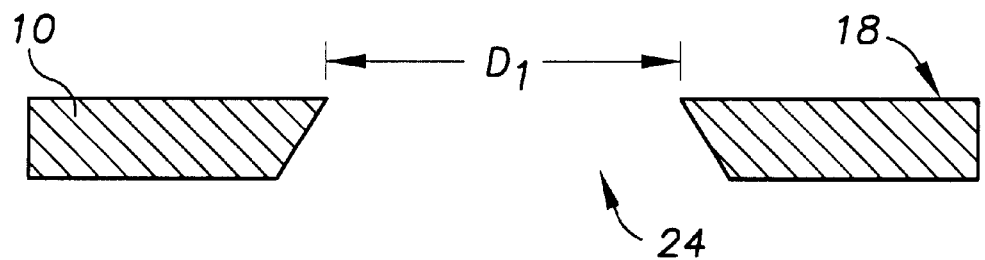
FIGS. 6A–6C are schematic cross-sectional views of stages in the reduction of a limiting aperture diameter by a process provided by the invention.
Figure 6B:
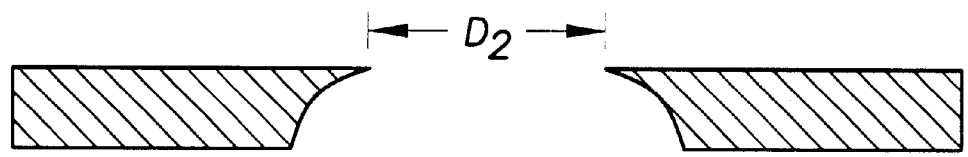
Figure 6C:
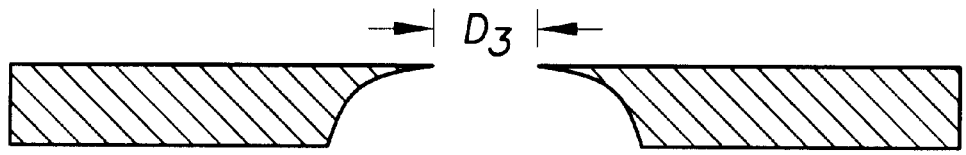

Referring to FIGS. 6A–6C, in a first example of this ion beam feature control, a limiting aperture 24 in a structure 10 is caused to be adjusted from a first diameter, $D_1$, to a smaller diameter, $D_2$ or $D_3$. The starting aperture is formed in a selected structure in any suitable fashion, e.g., by the methods described above and shown in FIGS. 1A–1D and FIGS. 2A–2G, in, e.g., a membrane, layer, substrate, or other structure. The structure surface 18 in which the limiting aperture was formed is then exposed to ion beam irradiation, employing, e.g., the system described above and illustrated in FIGS. 3A–3B.

As shown most dramatically in FIG. 6C, for selected ion beam irradiation conditions, the inventors have discovered the unexpected result that the material is added to the periphery, or boundary, of the limiting aperture 24 exposed to the irradiation, causing the diameter of the limiting aperture to decrease. This condition can be predictably and precisely imposed by enforcing structure temperature, ion flux rate, and ion energy conditions conducive to material addition at the aperture rim. Given that the ion beam irradiation is generally considered to be a sputtering/material removal process, it is particularly unexpected that this material movement and addition condition can effectively progress, even in the presence of the atomic sputtering erosion, to result in a change in the physical dimensions of a feature.

EXAMPLE 3

Figure 7A:
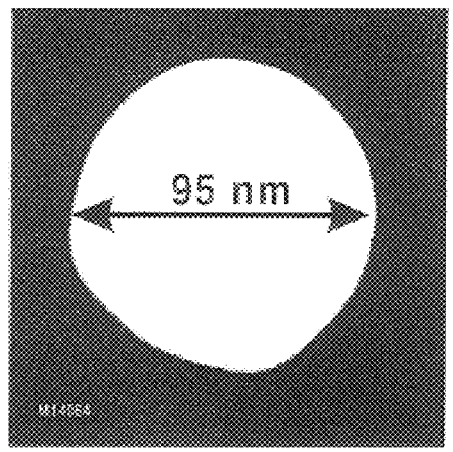
FIG. 7A is an electron micrograph of a 95 nm-wide aperture formed in a 500 nm-thick silicon nitride membrane in accordance with the invention.

A silicon nitride membrane of about 500 nm in thickness was produced in the manner of the process outlined in FIGS. 2A–E. An aperture was formed through the entire thickness of the membrane by reactive ion etching. FIG. 7A is an electron micrograph of the 95 nm-wide aperture that resulted from the etch.

The membrane and its aperture were then exposed to an argon ion beam flux at an energy of about 3 KeV, and a flux of about 47 $Ar^+/sec/nm^2$. The membrane was maintained at a temperature of about 20° C. during ion flux exposure. The ion beam was directed to the membrane for 250 ms for each 1 sec time interval.

Figure 7B:
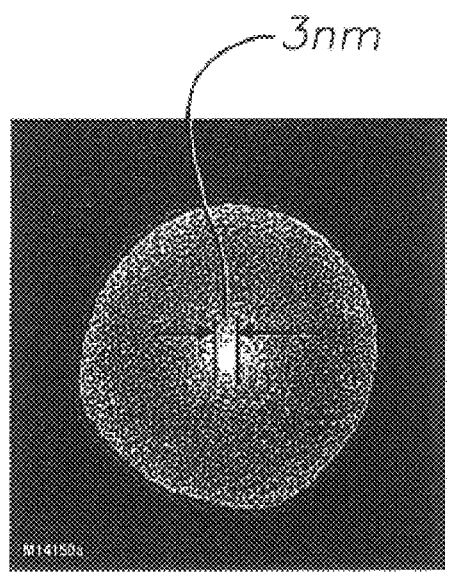
FIG. 7B is an electron micrograph of the aperture of FIG. 6A reduced to 3 nm in width by a process provided by the invention.
Figure 7C:
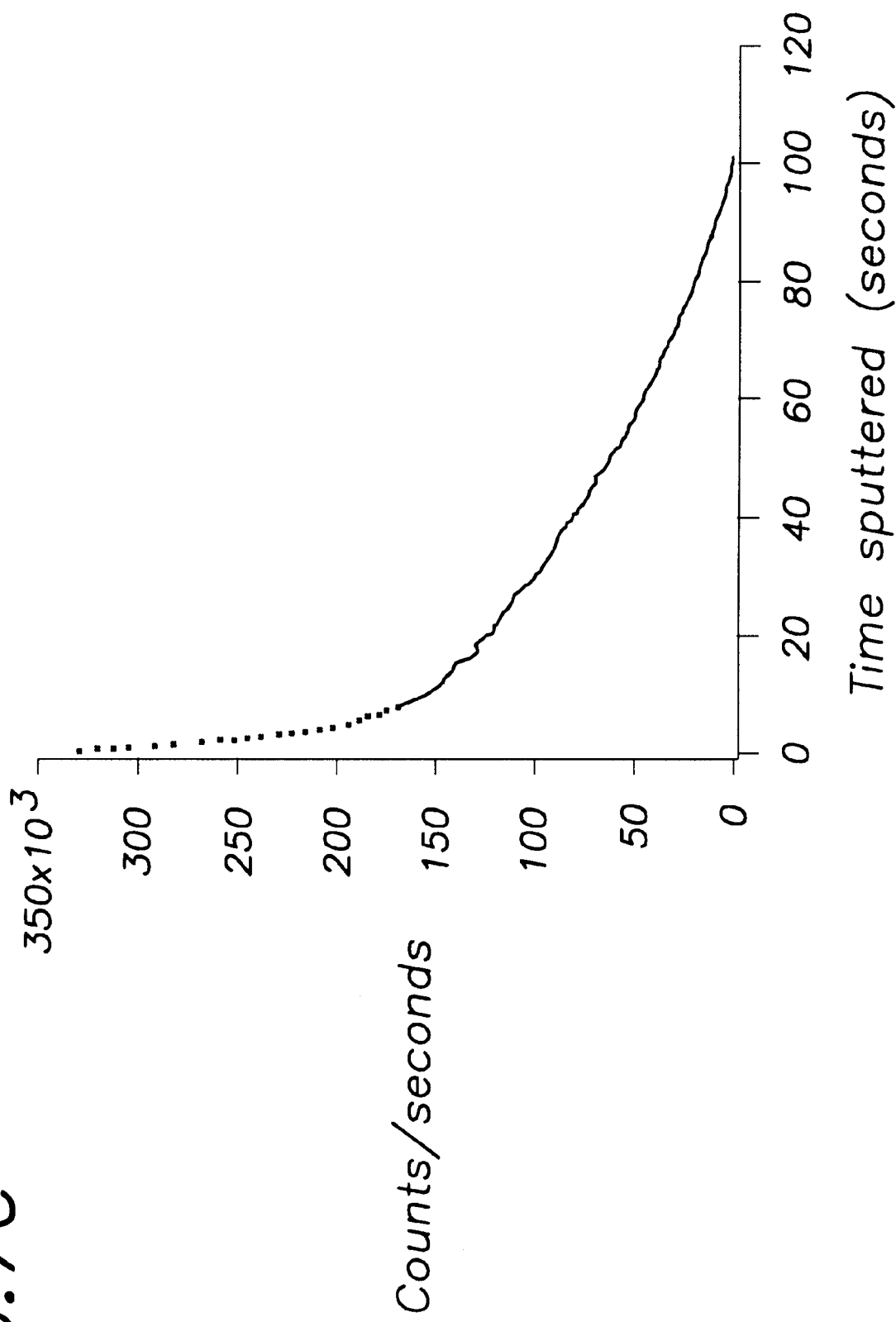
FIG. 7C is a plot of detected ion counts as a function of time for the aperture etch process that resulted in the aperture decrease from that shown in FIG. 7A to that shown in FIG. 7B.

FIG. 7B is an electron micrograph of the membrane after exposure to the argon ion beam reduced the aperture diameter to about 3 nm. FIG. 7C is a plot of counted argon ions/sec as a function of time. A generally linear count rate is indicated for midpoints in the process.

Without being bound by theory, the inventors herein understand that the mechanisms underlying the ability of an ion beam to cause material build up at an ion-irradiated aperture rim may be related to atomic transport through the bulk of the structure; ion-induced changes in viscosity, electronic surface charge, mechanical stress generation, and lateral swelling of the structure; and/or atomic surface transport caused by ion-induced surface atom excitation or supersaturation of mobile adsorbed ionic species on the structure surface. At sufficiently low ion energies the ion penetration depth is much less than the structure thickness, resulting in a domination of surface transport processes. The invention does not require a specific material transformation mechanism, but rather, provides distinguishing process control parameters that impose predictable material transformation results.

Considering the process parameters to be controlled, it is found that the temperature of the structure being exposed to the ion beam irradiation directly impacts the ability to impose material movement and the rate at which material moves. It is found that for a specific structural material, there is a characteristic temperature above which material of the structure is found to move, resulting in an adjustment, or change, in feature dimensions and below which material is instead removed by sputtering from the structure. For given ion beam energy and flux conditions, control between material removal and dimensional feature adjustment can therefore be imposed by structural temperature control.

EXAMPLE 4

Figure 8:
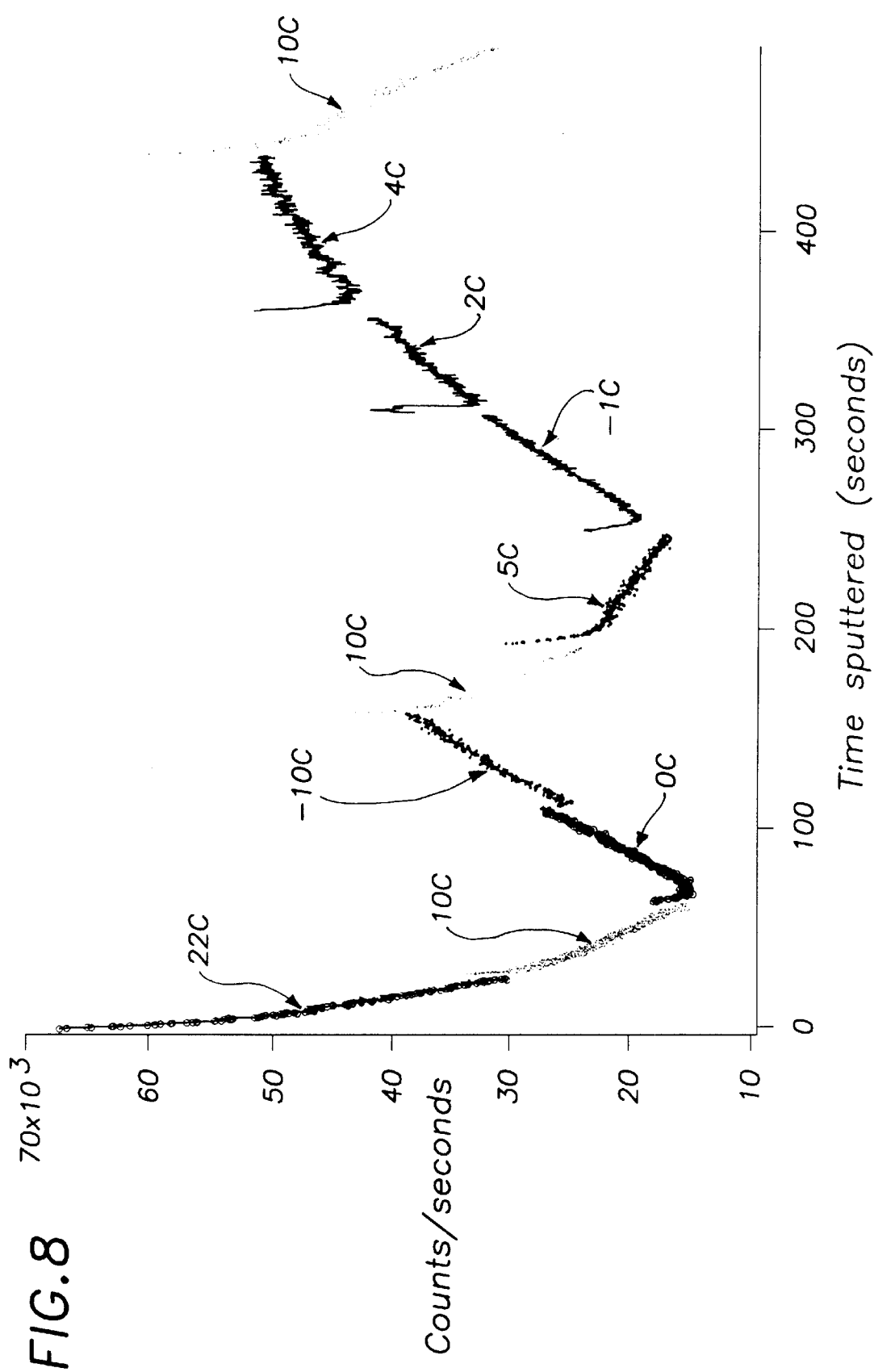
FIG. 8 is a plot of detected ion counts per second as a function of ion sputtering time of a square aperture, initially of about 72 nm×72 nm in area, in a silicon nitride membrane of 500 nm in thickness, subjected to the mass transport processes of the invention under various temperatures.

Referring to the graph of FIG. 8, there is plotted the ion counts/second detected by an ion sputtering system like that of FIG. 3A as a function of time for a 500 nm-thick silicon nitride membrane in which was initially fabricated a square aperture of about 72 nm in length. The membrane was fabricated based on the process shown in FIGS. 2A–2F and the aperture was fabricated by a focussed ion beam directed at the membrane to form an aperture that extended completely through the membrane. Each region of the graph indicates the temperature at which the membrane was maintained during bombardment by an argon ion beam. The beam flux was 14 $Ar^+/sec/nm^2$ and the beam energy was 3 KeV. The on/off duty cycle of the ion beam being directed toward the membrane was such that the beam was directed to the membrane for 200 msec during each 1 sec interval.

As a function of time, an increase in ion count/second indicates an increase in the aperture dimension, while a decrease in ion count/second indicates a decrease in the aperture dimension. The plotted data clearly indicate an increasing rate of aperture shrinkage under the ion beam irradiation as the membrane temperature is increased above about 5° C. In contrast, at membrane temperatures below about 4° C. the aperture dimension increases rather than decreases. At membrane temperatures between about 0° C. and about −10° C. no appreciable temperature dependence in the rate at which the aperture dimension decreases is indicated.

With this experimental data, it is indicated that for a silicon nitride membrane, two distinct temperature regimes exist; the first temperature regime, at or above about 5° C., imposes material movement and feature addition by ion beam irradiation, the second temperature regime, at or below about 4° C., imposes material sputtering and removal by ion beam irradiation, both regimes for given ion beam species, flux, and energy conditions. This analysis for a silicon nitride membrane is an example of the empirical analysis contemplated by the invention to determine that temperature above which a material of interest can be made to move and augment features. It is recognized that this transition temperature can vary widely from material to material.

The plotted data also indicate that within the regime for imposing material movement and addition, the rate of material transport in altering feature topology is temperature dependent. At relatively higher temperatures, the transport process proceeds more rapidly than at relatively lower temperatures. Knowledge of this temperature-dependent transport rate enables precise process control and characterization.

EXAMPLE 5

Five silicon nitride membranes of about 500 nm were fabricated in the manner of the process outlined in FIGS. 2A–E. Apertures each of about 1400 $nm^2$ in area were produced in the membranes by focused ion beam etching.

The membranes were then exposed to an argon ion beam at an energy of about 3 KeV for various total doses at five ion beam fluxes. Each membrane was maintained at a temperature of about 22° C. during the ion beam exposure. Each ion beam exposure was controlled to sputter for 200 msec during each 1 second interval.

Figure 9A:
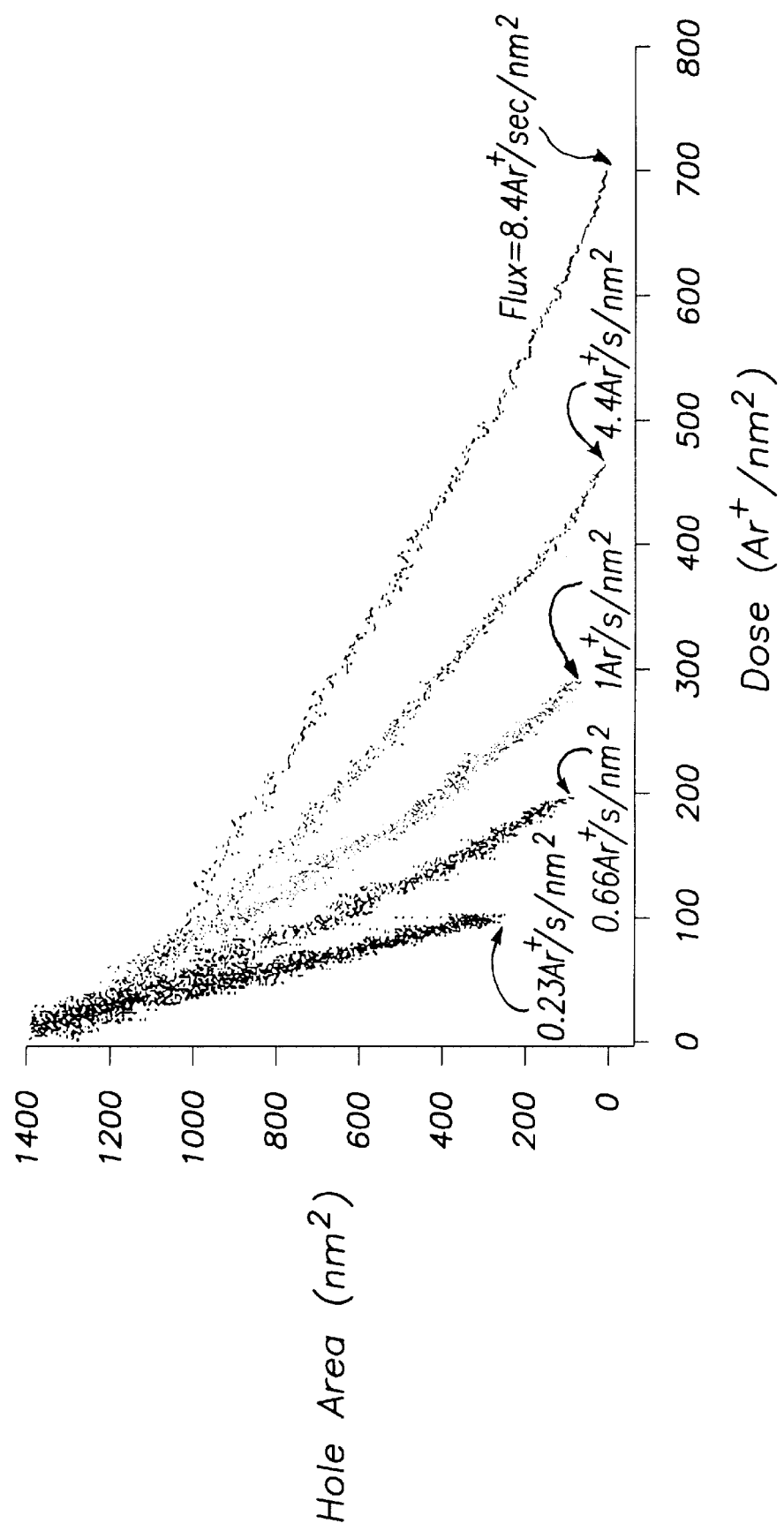
FIGS. 9A–9B are plots of aperture area as a function of total ion dose for five different ion fluxes and aperture area decrease per dose as a function of ion flux, respectively, for an aperture having an initial area of about 1400 nm$^2$, for the material transport processes provided by the invention.
Figure 9B:
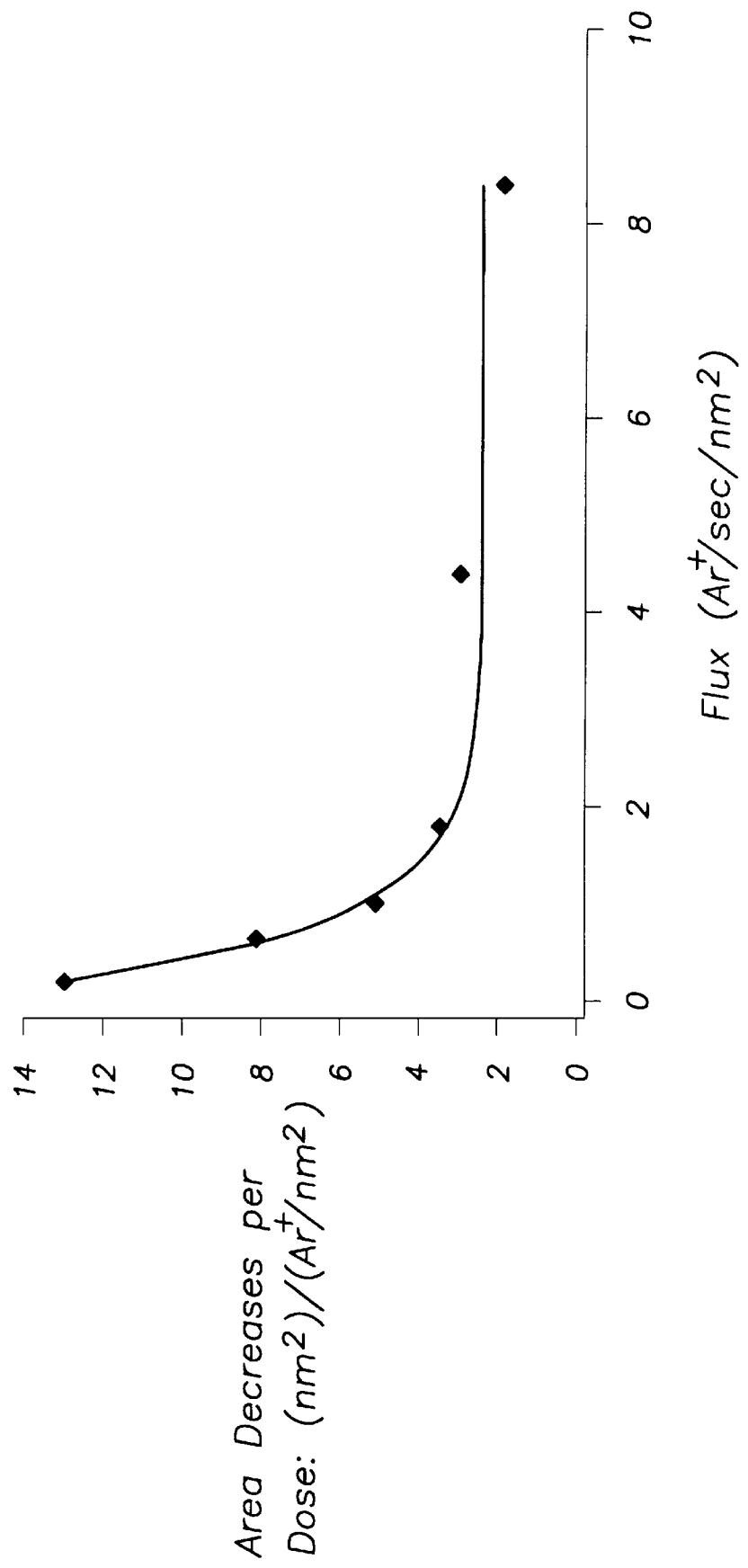

Referring to the graphs of FIGS. 9A–9B, there is plotted the area of the apertures in $nm^2$ as a function of total argon ion beam dose, in $ions/nm^2$, for five different argon ion beam fluxes, and the aperture area decrease per dose, as a function of argon ion beam flux, respectively. From the plotted data, it is indicated that as a function of total argon ion beam dose, the aperture shrinks more rapidly at low incident fluxes relative to higher incident fluxes. In other words, the lower the flux, the less dose is required to shrink an aperture. The strong nonlinearity indicates that the amount of material mass transport produced by the ion beam irradiation per incident ion may be suppressed at high incident fluxes. This characterization enables operation at a selected mass transport rate. In a manner analogous to the temperature dependence analysis provided above, the invention contemplates empirical analysis of flux dependence for a selected material, to enable precise control of the material movement.

EXAMPLE 6

Figure 10A:
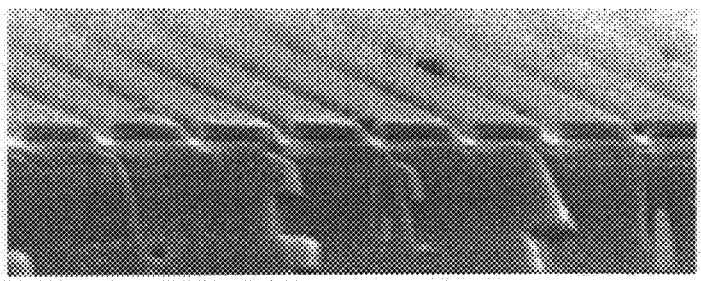
FIGS. 10A–10C are scanning electron micrographs of a trenched silicon nitride layer exposing the underlying silicon wafer on which the layer was deposited, partial fill-in of the silicon nitride trenches as a result of the material transport process conditions provided by the invention, and partial sputter etch removal of the upper trench layer as a result of the sputtering conditions provided by the invention.

A 50 nm-thick layer of silicon nitride was deposited by low pressure chemical vapor deposition on a silicon wafers. The silicon nitride layer was patterned by electron beam lithography to produce trenches of about 50 nm in width through the entire thickness of the silicon nitride layer. The bottom of each trench thereby exposed the underlying silicon surface. FIG. 10A is a scanning electron micrograph of the trenched silicon nitride layer on the silicon wafer.

Figure 10B:
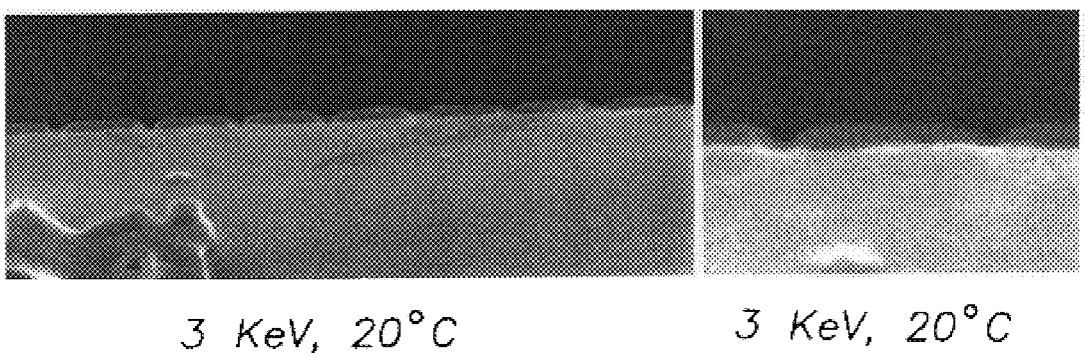

The trenched silicon nitride layer was exposed to an argon ion beam at an energy of about 3 KeV and a flux of about 20 $Ar^+/nm^2/sec$, where the ion beam was sputtering for 0.5 seconds for each 2 second interval. The silicon wafer was maintained at a temperature of about 20° C. during the ion beam exposure. FIG. 10B is a scanning electron micrograph of the trenched silicon nitride layer after about 200 seconds of sputtering. Note that silicon nitride material has been moved to the trenches, whereby the trenches have been partially filled in. This indicates that for the process conditions here employed, material is transported from the silicon nitride layer to the trenches.

Figure 10C:
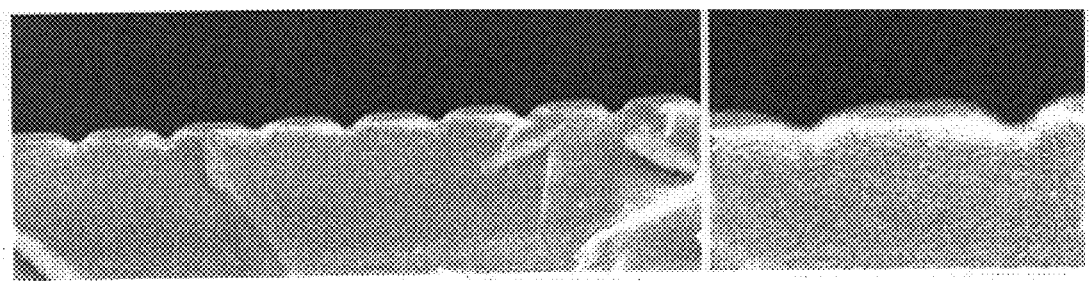

A second 50 nm-thick trenched silicon nitride layer like the one just described was exposed to an argon ion beam at an energy of about 3 KeV and an ion flux of about 30 $Ar^+/nm^2/sec$, with the ion beam sputtering for one second during each two second interval, for a total sputtering time of about 300 seconds. The silicon wafer was maintained at a temperature of about −100° C. during the ion beam exposure. FIG. 10C is a scanning electron micrograph of the trenched silicon nitride layer. Here, the silicon nitride material at the top of the trenches has been etched away, as indicated by the rounding of the trench edges, but the bottom of the trenches are not at all filled in.

This example demonstrates the temperature control that can be imposed to predictably produce material transport and feature adjustment or material removal by sputtering as desired for a given application.

Turning to additional material transport control mechanisms provided by the invention, it is understood that the energy of the ion beam can impact the nature of material transport. Specifically, for a given structural material and temperature, a given ion beam current density, and a given time structure of the ion beam exposure, as discussed below, there exists an ion beam energy above which material transport is effectively induced in the manner described above and below which sputtering in the conventional manner occurs. This juncture between the two distinct operational regimes can be empirically determined for a given material and ion beam exposure system, and can be employed as an important control technique for precisely enabling and disabling the material transport processes.

Further in accordance with the invention, it is found that the time structure of the ion flux exposure, i.e., the sequence of intervals in which the ion beam is controlled to enable interaction with a material and then controlled to not interact with the material, impacts the nature of material transport and dimensional feature change. Specifically, the imposition of an on/off duty cycle on the ion flux is found to impact the ability to cause material movement and corresponding dimensional feature change.

EXAMPLE 7

A 500 nm-thick silicon nitride membrane was produced in the manner of the process outlined in FIGS. 2A–E. A 95 nm-wide aperture was formed through the entire thickness of the membrane by focused ion beam etch. The membrane and aperture were then exposed to an argon ion beam at an energy of about 3 KeV and a flux of about 14 $Ar^+/sec/nm^2$. The membrane was maintained at a temperature of about 16° C. during the ion beam exposure. During the exposure, the amount of time that the ion beam was directed to the membrane was varied. Six different time structures were employed: 100 msec on for each 1 second interval; 200 msec on for each 1 second interval; 400 msec on for each 1 second interval; 600 msec on for each 1 second interval; 600 msec on for each 2 second interval; and 600 msec on for each 4 second interval. During the ion beam exposure, ion detection and counting was carried out as an indication of the reduction or enlargement of the aperture in response to the various ion beam exposure cycles.

Figure 11:
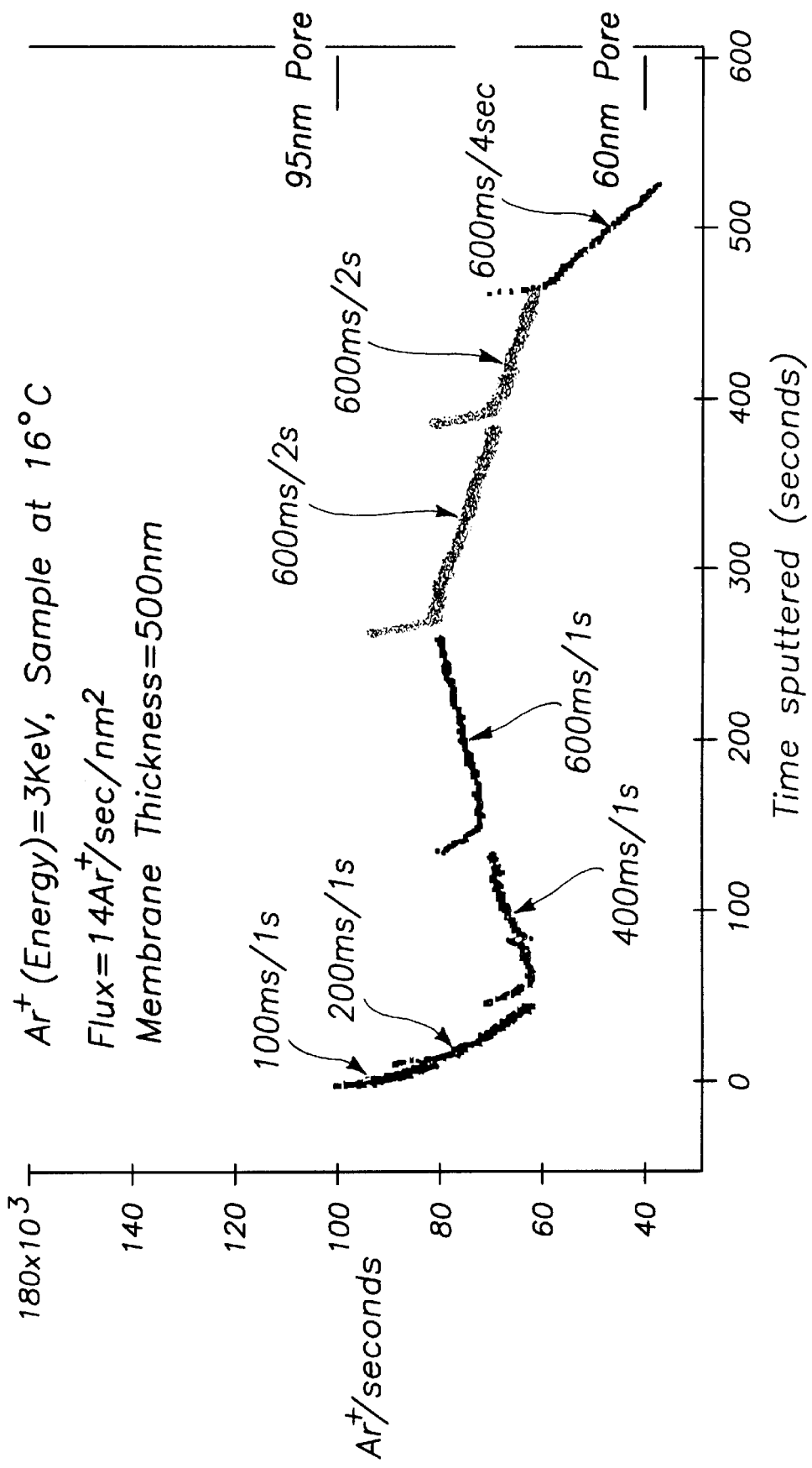
FIG. 11 is a plot of counted ions/second traversing an aperture as a function of time for various ion beam exposure cycles.

FIG. 11 is a plot of argon ions counted/second as a function of sputtered time. The plot indicates that the 400 msec/1 second interval and the 600 msec/1 second interval time structures increased the aperture diameter, while all other time structures decreased the aperture diameter. This demonstrates that at about room temperature, control between material transport processes and sputtering processes can be achieved by control of the ion beam exposure time structure.

The ion detection and counting mechanism of the invention for imposing feedback control on ion irradiation mass transport is advantageous for many applications for enabling precise feature formation, but is not required by the invention. Once a mass transport process is characterized, and for processes that do not require very fine feature control, feedback control of the system may not be required. All that is required is the exposure of the material to an ion beam under conditions that impose processes such as mass transport for adjusting dimensions of structural features of the material by local material addition or subtraction.

This structural material adjustment process provided by the invention can be applied to a wide range of structural features, including holes, slits, apertures, and gaps in general, and in trenches and other such features where a distinct feature rim or wall is present and can be adjusted. It further can be applied to fabrication of protruding features such as hillocks and asperities.

In one example of such a fabrication technique, the ion flux and dose and the temperature of a membrane are selected to produce a protrusion on the membrane by exposure to ion beam flux. One membrane surface is exposed to the ion beam flux under the selected conditions. This results in formation of a protrusion on the membrane surface opposite that exposed to the ion flux.

EXAMPLE 8

A silicon nitride membrane of about 500 nm in thickness was produced by a LPCVD process following the fabrication sequence outlined in FIG. 2. The membrane was exposed to a gallium ion beam at an energy of about 50 KeV and a dose of about 4 nanocoulombs/$\mu m^2$. Five different isolated exposure areas on the membrane were defined, namely, 0.12 $\mu m^2$, 0.14 $\mu m^2$, 0.16 $\mu m^2$, 0.18 $\mu m^2$, and 0.20 $\mu m^2$.

Figure 12:
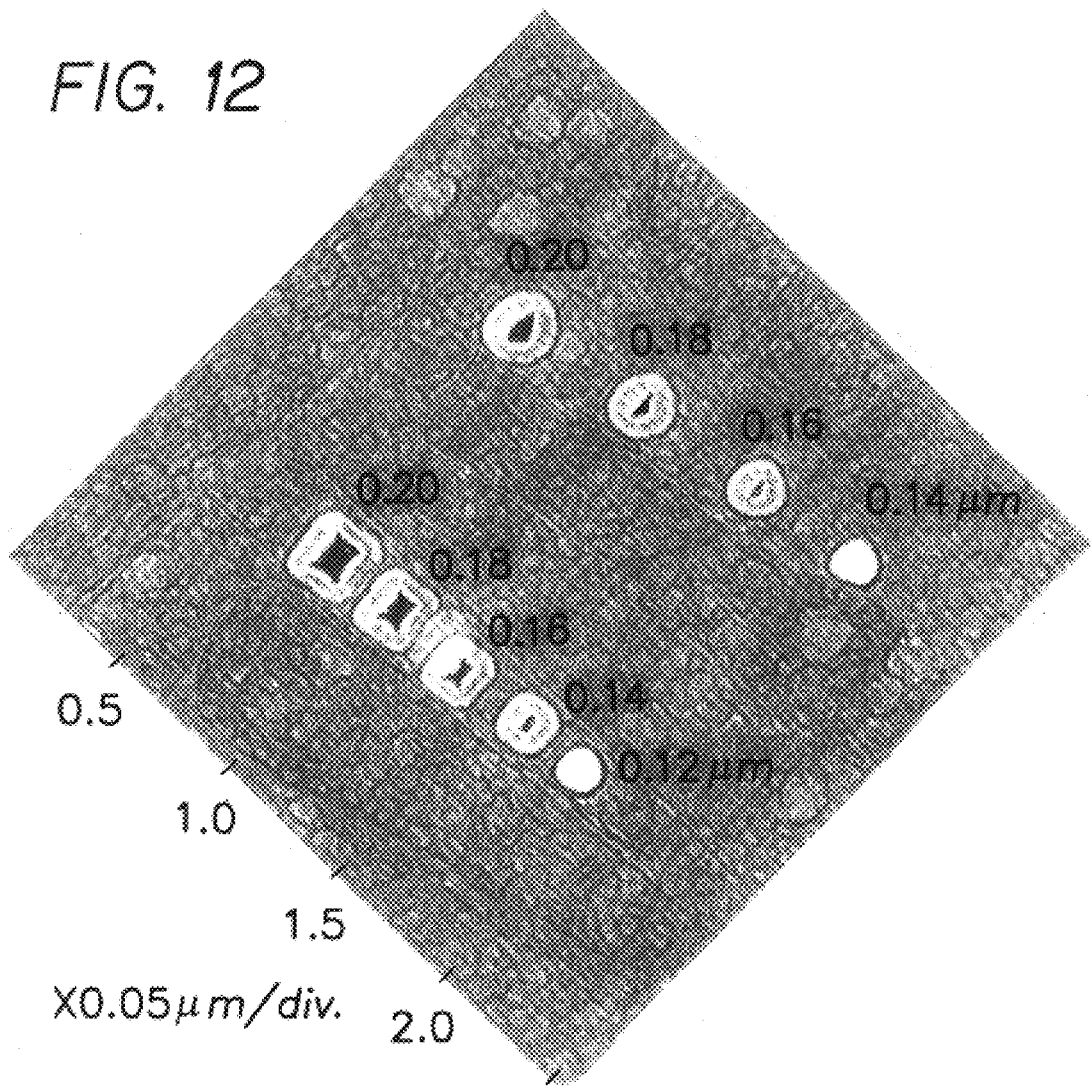
FIG. 12 is an atomic force micrograph of a silicon nitride membrane one surface of which was exposed to a focused ion beam to produce apertures and protrusions on the membrane surface opposite that exposed to the ion beam.

FIG. 12 is an atomic force micrograph of the nitride membrane surface opposite that which was exposed to the gallium ion beam. In this image, brightness level corresponds to topology; the brighter a region in the image, the "taller," or higher, is the topology of that region. As noted in the image, both of the 0.16 $\mu m^2$, 0.18 $\mu m^2$, and 0.20 $\mu m^2$ membrane areas, and one of the 0.14 $\mu m^2$ membrane areas were opened by the ion beam exposure, i.e., an aperture through the thickness of the membrane resulted from the ion beam exposure in that area. The other 0.14 $\mu m^2$ membrane area and the 0.12 $\mu m^2$ membrane area were not opened by the ion beam exposure and instead exhibit hill-like protrusions formed on the membrane surface opposite that exposed to the ion beam. This example demonstrates that dose can be controlled to cause mass transport in a manner that produces a protrusion on the surface of a structure. This example further demonstrates that the ion beam species can impact the nature of feature formation and adjustment; in this example gallium ions were employed as opposed to the argon ions employed in earlier examples. It is understood in accordance with the invention that ion species can be selected to control aspects of feature formation processing. Similarly, it is understood in accordance with the invention that the ambient gas species present during the ion interaction with a material can be selected to control the nature of the interaction.

The features formed by and/or having dimensions adjusted or changed by the processes of the invention can be provided on the surface of a structure, in a layer provided on a support structure or a free-standing membrane, or other surface which can be irradiated by an ion beam. Composite material structures can be processed. There is no restriction on the fabrication sequence employed to produce the starting structures for which dimensional adjustment is to be carried out.

This discussion highlights the wide range of applications of the solid state feature formation and dimensional control processes of the invention. Molecular sensing techniques, microfabrication mask formation, and electronic device electrode formation and adjustment are a few of the many applications. The subtractive and additive materials processing techniques of the invention, in conjunction with the physical species detection and feedback control of the invention, enable reproducible and highly precise feature formation. The advantages of this precision and control are most apparent when applied to nanometric feature dimensions and dimensional tolerances. It is recognized, of course, that those skilled in the art may make various modifications and additions to the processes of the invention without departing from the spirit and scope of the present contribution to the art. Accordingly, it is to be understood that the protection sought to be afforded hereby should be deemed to extend to the subject matter of the claims and all equivalents thereof fairly within the scope of the invention.

We claim:

1. A method for controlled fabrication of a solid state structural feature, comprising the steps of:
   providing a solid state structure;
   exposing the structure to a fabrication process environment the conditions of which are selected to produce a prespecified feature in the structure;
   directing a physical detection species toward a designated structure location during process environment exposure of the structure;
   detecting the detection species in a trajectory from the designated structure location, to indicate changing physical dimensions of the prespecified feature; and
   controlling the fabrication process environment in response to physical species detection to fabricate the structural feature.

2. The method of claim 1 wherein the structure comprises a substrate of inorganic material.

3. The method of claim 1 wherein the structure comprises a substrate of crystalline material.

4. The method of claim 3 wherein the crystalline substrate comprises a semiconductor wafer.

5. The method of claim 1 wherein the structure comprises a membrane.

6. The method of claim 1 wherein the structure comprises a substrate including a layer in which the prespecified feature is to be fabricated.

7. The method of claim 1 wherein the structure comprises an organic substrate.

8. The method of claim 1 wherein the fabrication process environment is a sputtering environment.

9. The method of claim 8 wherein the fabrication process environment is an ion beam sputtering environment.

10. The method of claim 8 wherein the fabrication process environment is an electron beam sputtering environment.

11. The method of claim 1 wherein the fabrication process environment is a wet chemical etch environment.

12. The method of claim 11 wherein the fabrication process environment is an electrochemical etch environment.

13. The method of claim 1 wherein the fabrication process environment is a plasma environment.

14. The method of claim 1 wherein the fabrication process environment is a chemomechanical polishing environment.

15. The method of claim 1 wherein the fabrication process environment comprises an ion-assisted fabrication process.

16. The method of claim 1 wherein the fabrication process environment comprises an ion-induced fabrication process.

17. The method of claim 1 wherein the fabrication process environment is a material deposition environment.

18. The method of claim 1 wherein the fabrication process environment is a material growth environment.

19. The method of claim 1 wherein the fabrication process environment is a heating environment.

20. The method of claim 1 wherein the prespecified feature is an aperture, the fabrication process conditions are selected to etch the aperture in the structure, and the detection species trajectory is through the aperture.

21. The method of claim 20 wherein the prespecified feature comprises an array of apertures.

22. The method of claim 1 wherein the prespecified feature is an aperture, the fabrication process conditions are selected to enlarge aperture diameter, and the detection species trajectory is through the aperture.

23. The method of claim 1 wherein the prespecified feature is an aperture, the fabrication process conditions are selected to reduce aperture diameter, and the detection species trajectory is through the aperture.

24. The method of claim 1 wherein the prespecified feature is a trench, the fabrication process conditions are selected to etch the trench in the structure, and the detection species trajectory is through the trench.

25. The method of claim 1 wherein the prespecified feature is a trench, the fabrication process conditions are selected to reduce trench width, and the detection species trajectory is through the trench.

26. The method of claim 1 wherein the prespecified feature is a gap between at least two structural edges, the fabrication process conditions are selected to enlarge the gap, and the detection species trajectory is through the gap.

27. The method of claim 1 wherein the prespecified feature is a gap between at least two structural edges, the fabrication process conditions are selected to reduce the gap, and the detection species trajectory is through the gap.

28. The method of claim 1 wherein the prespecified feature is a slot, the fabrication process conditions are selected to etch the slot in the structure, and the detection species trajectory is through the slot.

29. The method of claim 1 wherein the detection species comprises atoms.

30. The method of claim 1 wherein the detection species comprises ions.

31. The method of claim 1 wherein the detection species comprises electrons.

32. The method of claim 1 wherein the detection species comprises an etch species provided in the selected fabrication process environment.

33. The method of claim 1 wherein the step of detecting the detection species comprises detecting existence of detection species in a trajectory from traversal of the designated structure location.

34. The method of claim 33 wherein the step of detecting the detection species further comprises quantifying detection species as a function of time.

35. The method of claim 1 wherein the step of controlling the fabrication process environment comprises terminating exposure of the structure to the process environment at a point in time when the species detection indicates fabrication of prespecified dimensions of the structural feature.

36. A method for fabricating an aperture in a solid state structure comprising the steps of:
providing a solid state structure having a first surface and an opposing second surface;
forming on the first structure surface a cavity extending to a cavity bottom located at a point between the first and second structure surfaces;
thinning the structure from the second structure surface;
directing a physical detection species toward a location on the structure for the aperture as defined by the cavity, during the structure thinning;
detecting the physical detection species in a trajectory through the aperture when thinning of the structure causes the second structure surface to intersect with the cavity bottom; and
controlling the structure thinning based on physical detection species detection.

37. The method of claim 36 further comprising the steps of:
quantifying the detected physical detection species during the structure thinning; and
controlling the structure thinning based on physical detection species quantification to produce an aperture of a prespecified diameter.

38. The method of claim 36 wherein the structure comprises a membrane.

39. The method of claim 38 wherein the structure comprises a silicon nitride membrane.

40. The method of claim 36 wherein the step of structure thinning comprises sputtering.

41. The method of claim 36 wherein the detection species comprises ions.

42. The method of claim 36 wherein the detection species comprises electrons.

43. The method of claim 36 where the detection species is distinct from a species provided for thinning the structure.

44. The method of claim 36 wherein the detection species is a species provided for thinning the structure.

45. A method for controlling a physical dimension of a solid state structural feature comprising the steps of:
providing a solid state structure having a surface and having a structural feature; and
exposing the structure to a flux of ions at a selected structure temperature, ion flux exposure conditions being selected to cause transport, within the structure including the structure surface, of material of the structure to the structural feature in response to ion flux exposure to change at least one physical dimension of the feature substantially by locally adding material of the structure to the feature.

46. The method of claim 45 wherein the change of at least one physical dimension of the feature substantially by material transport comprises an increase in feature dimensions.

47. The method of claim 45 further comprising the steps of:
directing a physical detection species toward the feature during ion flux exposure of the structure;
detecting the detection species in a trajectory from the feature, to indicate changing physical dimensions of the feature; and
controlling the ion flux exposure in response to physical species detection to change at least one physical dimension of the feature in a prespecified manner.

48. The method of claim 45 wherein the structure is a crystalline substrate.

49. The method of claim 48 wherein the crystalline substrate is a silicon nitride membrane.

50. The method of claim 45 wherein the feature is an aperture.

51. The method of claim 50 wherein change in aperture dimension comprises a reduction of aperture diameter.

52. The method of claim 45 wherein the feature is a trench.

53. The method of claim 52 wherein change in trench dimension comprises a reduction in trench width.

54. The method of claim 45 wherein the feature is a gap between at least two edges.

55. The method of claim 54 wherein change in gap dimension comprises a reduction in gap width.

56. The method of claim 45 wherein the ion flux comprises flux from a focused ion beam.

57. A method for fabricating a feature on a solid state structure comprising the steps of:
providing a solid state structure having a surface; and
exposing the structure to a flux of ions at a selected structure temperature, ion flux exposure conditions being selected to cause transport, within the structure including the structure surface, of material of the structure to a feature location in response to the ion flux exposure to produce the feature substantially by locally adding material of the structure to the feature location.

58. The method of claim 57 wherein the structure comprises a membrane.

59. The method of claim 57 wherein the feature is a protrusion.

60. The method of claim 57 wherein the step of exposing the structure to a flux of ions comprises exposing a first membrane surface to the ion flux to produce a protrusion on a second membrane surface opposite the first membrane surface.

61. The method of claim 60 wherein the membrane comprises a silicon nitride membrane.

62. The method of either of claims 45 or 57 wherein the exposure condition selection comprises control of structure temperature.

63. The method of either of claims 45 or 57 wherein the exposure condition selection comprises control of ion flux.

64. The method of either of claims 45 or 57 wherein the exposure condition selection comprises control of ion energy.

65. The method of either of claims 45 or 57 wherein the exposure condition selection comprises control of ion flux time structure.

66. The method of either of claims 45 or 57 wherein the exposure condition selection comprises control of ion species.

67. The method of either of claims 45 or 57 wherein the exposure condition selection comprises control of ambient gas species.

68. The method of either of claims 45 or 57 wherein the feature comprises a geometric feature in a lithographic mask.

69. The method of claim 68 wherein the geometric mask feature comprises a wire geometry.

70. The method of claim 68 wherein the geometric mask feature comprises a pad geometry.

71. The method of claim 57 wherein the feature comprises a boundary.

72. The method of claim 57 wherein the feature comprises a structural feature.

73. A method for controlled fabrication of a solid state structural feature, comprising the steps of:

providing a solid state structure;

exposing the structure to a fabrication process environment the conditions of which are selected to produce a prespecified feature in the structure;

directing a physical detection species toward a designated structure location during process environment exposure of the structure;

measuring changing physical dimensions of the prespecified feature by detecting the detection species in a trajectory from the designated structure location; and controlling the fabrication process environment in response to physical species detection to fabricate the structural feature.

74. A method for controlling a dimension of a feature of a solid state structure comprising the steps of:

providing a solid state structure having a surface and having a feature; and exposing the structure to a flux of ions at a selected structure temperature, ion flux exposure conditions being selected to cause transport, within the structure including the structure surface, of material of the structure to the feature in response to the ion flux exposure to change at least one dimension of the feature substantially by locally adding material of the structure to the feature.

75. A method for controlling a physical dimension of a solid state structural feature comprising the steps of:

providing a solid state structure having a surface and having a structural feature with an edge boundary; and exposing the structure to a flux of ions at a selected structure temperature, ion flux exposure conditions being selected to cause transport, within the structure including the structure surface, of material of the structure to the structural feature edge boundary in response to the ion flux exposure to change at least one physical dimension of the feature substantially by locally adding material of the structure to the feature edge boundary.

76. A method for controlling a dimension of a feature of a solid state structure comprising the steps of:

providing a solid state structure having a surface;

forming in the solid state structure a feature;

transporting, within the structure including the structure surface, material of the structure to the feature by exposure of the structure to a flux of ions to change at least one dimension of the feature substantially by locally adding material of the structure to the feature.

77. A method for controlling a physical dimension of a solid state structural feature comprising the steps of:

providing a solid state structure having a surface;

forming in the solid state structure a structural feature;

transporting, within the structure including the structure surface, material of the structure to the feature by exposure of the structure to a flux of ions to change at least one physical dimension of the feature substantially by locally adding material of the structure to the feature.

78. A method for controlling a physical dimension of a solid state structural feature comprising the steps of:

providing a solid state structure having a surface;

forming in the solid state structure a structural feature having an edge boundary;

transporting, within the structure including the structure surface, material of the structure to the feature edge boundary by exposure of the structure to a flux of ions to change at least one physical dimension of the feature substantially by locally adding material of the structure to the feature edge boundary.

* * * * *